(12) United States Patent
Strother et al.

(10) Patent No.: US 8,195,304 B2
(45) Date of Patent: Jun. 5, 2012

(54) IMPLANTABLE SYSTEMS AND METHODS FOR ACQUISITION AND PROCESSING OF ELECTRICAL SIGNALS

(75) Inventors: Robert B. Strother, Willoughby Hills, OH (US); Joseph J. Mrva, Euclid, OH (US); Geoffrey B. Thrope, Shaker Heights, OH (US)

(73) Assignee: Medtronic Urinary Solutions, Inc., Minneapolis, MN (US)

( * ) Notice: Subject to any disclaimer, the term of this patent is extended or adjusted under 35 U.S.C. 154(b) by 1141 days.

(21) Appl. No.: 11/974,279

(22) Filed: Oct. 12, 2007

(65) Prior Publication Data

US 2008/0132974 A1  Jun. 5, 2008

Related U.S. Application Data

(63) Continuation of application No. 11/150,734, filed on Jun. 10, 2005, now Pat. No. 7,283,867.

(60) Provisional application No. 60/578,742, filed on Jun. 10, 2004, provisional application No. 60/599,193, filed on Aug. 5, 2004, provisional application No. 60/680,598, filed on May 13, 2005.

(51) Int. Cl.
*A61N 1/08* (2006.01)
*A61B 19/00* (2006.01)

(52) U.S. Cl. .......................................... 607/60
(58) Field of Classification Search ............. 607/32–33, 607/59–61
See application file for complete search history.

(56) References Cited

U.S. PATENT DOCUMENTS

| | | | |
|---|---|---|---|
| 3,421,511 A | 1/1969 | Schwartz et al. |
| 3,654,933 A | 4/1972 | Hagfors |
| 3,727,616 A | 4/1973 | Lenzkes |
| 3,774,618 A | 11/1973 | Avery |
| 3,870,051 A | 3/1975 | Brindley |
| 3,902,501 A | 9/1975 | Citron et al. |
| 3,926,198 A | 12/1975 | Kolenik |
| 3,939,841 A | 2/1976 | Dohring et al. |
| 3,939,843 A | 2/1976 | Smyth |
| 3,941,136 A | 3/1976 | Bucalo |
| 3,943,932 A | 3/1976 | Woo |
| 3,943,938 A | 3/1976 | Wexler |
| 4,232,679 A | 11/1980 | Schulman |

(Continued)

FOREIGN PATENT DOCUMENTS

CA  2121219  10/1995

(Continued)

OTHER PUBLICATIONS

U.S. Appl. No. 60/486,579, Jul. 2003, Loeb et al.

(Continued)

*Primary Examiner* — Carl H Layno
*Assistant Examiner* — Jessica Sarcione
(74) *Attorney, Agent, or Firm* — Shumaker & Sieffert, P.A.

(57) ABSTRACT

Improved assemblies, systems, and methods provide an electrical signal processor for acquisition and processing of electric signals from tissue. The electrical signal processor is sized and configured to be implanted in subcutaneous tissue. The electrical signal processor includes an electrically conductive case of a laser welded titanium material. Control circuitry is located within the case, the control circuitry including a rechargeable power source, a receive coil for receiving a first radio frequency wireless telemetry to recharge the power source, and an antenna for receiving a second radio frequency wireless telemetry for communication with the electrical signal processor.

8 Claims, 9 Drawing Sheets

U.S. PATENT DOCUMENTS

| | | | |
|---|---|---|---|
| 4,254,775 A | 3/1981 | Langer | |
| 4,257,423 A | 3/1981 | McDonald | |
| 4,262,678 A | 4/1981 | Stokes | |
| 4,398,545 A | 8/1983 | Wilson | |
| 4,406,288 A | 9/1983 | Horwinski et al. | |
| 4,407,303 A | 10/1983 | Akerstrom | |
| 4,512,351 A | 4/1985 | Pohndorf | |
| 4,519,404 A | 5/1985 | Fleischhacker | |
| 4,569,351 A | 2/1986 | Tang | |
| 4,573,481 A | 3/1986 | Bullara | |
| 4,585,005 A | 4/1986 | Lue et al. | |
| 4,585,013 A | 4/1986 | Harris | |
| 4,590,689 A | 5/1986 | Rosenberg | |
| 4,590,946 A | 5/1986 | Loeb | |
| 4,592,360 A | 6/1986 | Lesnick | |
| 4,602,624 A | 7/1986 | Naples et al. | |
| 4,607,639 A | 8/1986 | Tanagho et al. | |
| 4,628,942 A | 12/1986 | Sweeney et al. | |
| 4,649,936 A | 3/1987 | Ungar et al. | |
| 4,658,515 A | 4/1987 | Oatman | |
| 4,703,755 A | 11/1987 | Tanagho et al. | |
| 4,716,888 A | 1/1988 | Wesner | |
| 4,721,118 A | 1/1988 | Harris | |
| 4,739,764 A | 4/1988 | Lue et al. | |
| 4,741,341 A | 5/1988 | Marach | |
| 4,750,499 A | 6/1988 | Hoffer | |
| 4,771,779 A | 9/1988 | Tanagho et al. | |
| 4,793,353 A | 12/1988 | Borkan | |
| 4,835,372 A | 5/1989 | Gombrich | |
| 4,920,979 A | 5/1990 | Bullara | |
| 4,926,875 A | 5/1990 | Rabinovitz et al. | |
| 4,934,368 A | 6/1990 | Lynch | |
| 4,940,065 A | 7/1990 | Tanagho et al. | |
| 4,989,617 A | 2/1991 | Memberg et al. | |
| 5,095,905 A | 3/1992 | Klepinski | |
| 5,113,869 A | 5/1992 | Nappholz et al. | |
| 5,154,172 A | 10/1992 | Terry, Jr. et al. | |
| 5,215,086 A | 6/1993 | Terry, Jr. et al. | |
| 5,222,494 A | 6/1993 | Baker, Jr. | |
| D337,820 S | 7/1993 | Hooper et al. | |
| 5,235,980 A | 8/1993 | Varrichio et al. | |
| 5,257,634 A | 11/1993 | Kroll | |
| 5,265,608 A | 11/1993 | Lee et al. | |
| 5,282,845 A | 2/1994 | Bush et al. | |
| 5,289,821 A | 3/1994 | Swartz | |
| 5,300,107 A | 4/1994 | Stokes et al. | |
| 5,324,322 A | 6/1994 | Grill, Jr. et al. | |
| 5,330,515 A | 7/1994 | Rutecki et al. | |
| 5,335,664 A | 8/1994 | Nigashima | |
| 5,344,439 A | 9/1994 | Otten | |
| 5,369,257 A | 11/1994 | Gibbon | |
| 5,370,671 A | 12/1994 | Maurer et al. | |
| 5,397,338 A | 3/1995 | Grey et al. | |
| 5,400,784 A | 3/1995 | Durand et al. | |
| 5,411,537 A | 5/1995 | Munshi et al. | |
| 5,449,378 A | 9/1995 | Schouenborg | |
| 5,454,840 A | 10/1995 | Krakovsky et al. | |
| 5,461,256 A | 10/1995 | Yamada | |
| 5,476,500 A | 12/1995 | Fain et al. | |
| 5,480,416 A | 1/1996 | Garcia et al. | |
| 5,486,202 A | 1/1996 | Bradshaw | |
| 5,487,756 A | 1/1996 | Kallesoe et al. | |
| 5,505,201 A | 4/1996 | Grill, Jr. et al. | |
| 5,531,778 A | 7/1996 | Maschino et al. | |
| 5,540,730 A | 7/1996 | Terry et al. | |
| 5,562,717 A | 10/1996 | Tippey et al. | |
| 5,588,960 A | 12/1996 | Edwards et al. | |
| 5,607,461 A | 3/1997 | Lathrop | |
| 5,634,462 A | 6/1997 | Tyler et al. | |
| 5,645,586 A | 7/1997 | Meltzer | |
| 5,669,161 A | 9/1997 | Huang | |
| 5,683,432 A * | 11/1997 | Goedeke et al. | 607/32 |
| 5,683,447 A | 11/1997 | Bush et al. | |
| 5,690,693 A | 11/1997 | Wang et al. | |
| 5,702,431 A | 12/1997 | Wang et al. | |
| 5,713,939 A | 2/1998 | Nedungadi et al. | |
| 5,716,384 A | 2/1998 | Snell | |
| 5,722,482 A | 3/1998 | Buckley | |
| 5,722,999 A | 3/1998 | Snell | |
| 5,733,322 A | 3/1998 | Starkebaum | |
| 5,741,313 A | 4/1998 | Davis et al. | |
| 5,741,319 A | 4/1998 | Woloszko et al. | |
| 5,752,977 A | 5/1998 | Grevious et al. | |
| 5,755,767 A | 5/1998 | Doan et al. | |
| 5,759,199 A | 6/1998 | Snell | |
| 5,807,397 A | 9/1998 | Barreras | |
| 5,824,027 A | 10/1998 | Hoffer et al. | |
| 5,843,141 A | 12/1998 | Bischoff et al. | |
| 5,857,968 A | 1/1999 | Benja-Athon | |
| 5,861,015 A | 1/1999 | Benja-Athon | |
| 5,861,016 A | 1/1999 | Swing | |
| 5,899,933 A | 5/1999 | Bhadra et al. | |
| 5,919,220 A | 7/1999 | Stieglitz et al. | |
| 5,922,015 A | 7/1999 | Schaldach | |
| 5,938,596 A | 8/1999 | Woloszko et al. | |
| 5,948,006 A | 9/1999 | Mann | |
| 5,957,951 A | 9/1999 | Cazaux et al. | |
| 5,984,854 A | 11/1999 | Ishikawa et al. | |
| 6,004,662 A | 12/1999 | Buckley | |
| 6,016,451 A | 1/2000 | Sanchez-Rodarte | |
| 6,026,328 A | 2/2000 | Peckham et al. | |
| 6,055,456 A | 4/2000 | Gerber | |
| 6,055,457 A | 4/2000 | Bonner | |
| 6,061,596 A | 5/2000 | Richmond et al. | |
| 6,091,995 A | 7/2000 | Ingle et al. | |
| 6,125,645 A | 10/2000 | Horn | |
| 6,126,611 A | 10/2000 | Bourgeois et al. | |
| 6,166,518 A | 12/2000 | Echarri et al. | |
| 6,169,925 B1 | 1/2001 | Villaseca et al. | |
| 6,181,965 B1 | 1/2001 | Loeb et al. | |
| 6,181,973 B1 | 1/2001 | Ceron et al. | |
| 6,185,452 B1 | 2/2001 | Schulman et al. | |
| 6,200,265 B1 | 3/2001 | Walsh et al. | |
| 6,208,894 B1 | 3/2001 | Schulman et al. | |
| 6,212,431 B1 | 4/2001 | Hahn et al. | |
| 6,216,038 B1 | 4/2001 | Hartlaub et al. | |
| 6,240,316 B1 | 5/2001 | Richmond et al. | |
| 6,240,317 B1 | 5/2001 | Villaseca et al. | |
| 6,249,703 B1 | 6/2001 | Stanton | |
| 6,257,906 B1 | 7/2001 | Price et al. | |
| 6,266,557 B1 | 7/2001 | Roe et al. | |
| 6,275,737 B1 | 8/2001 | Mann | |
| 6,292,703 B1 | 9/2001 | Meier et al. | |
| 6,308,101 B1 | 10/2001 | Faltys et al. | |
| 6,308,105 B1 | 10/2001 | Duysens et al. | |
| 6,319,208 B1 | 11/2001 | Abita et al. | |
| 6,319,599 B1 | 11/2001 | Buckley | |
| 6,321,124 B1 | 11/2001 | Cigaina | |
| 6,338,347 B1 | 1/2002 | Chung | |
| 6,345,202 B2 | 2/2002 | Richmond et al. | |
| 6,360,750 B1 | 3/2002 | Gerber et al. | |
| 6,381,496 B1 | 4/2002 | Meadows et al. | |
| 6,409,675 B1 | 6/2002 | Turcott | |
| 6,432,037 B1 | 8/2002 | Eini et al. | |
| 6,442,432 B2 | 8/2002 | Lee | |
| 6,442,433 B1 | 8/2002 | Linberg | |
| 6,445,955 B1 | 9/2002 | Michelson et al. | |
| 6,449,512 B1 | 9/2002 | Boveja et al. | |
| 6,450,172 B1 | 9/2002 | Hartlaub et al. | |
| 6,453,198 B1 | 9/2002 | Torgerson et al. | |
| 6,456,866 B1 | 9/2002 | Tyler et al. | |
| 6,464,672 B1 | 10/2002 | Buckley | |
| 6,482,154 B1 | 11/2002 | Haubrich et al. | |
| 6,493,587 B1 | 12/2002 | Eckmiller et al. | |
| 6,493,881 B1 | 12/2002 | Picotte | |
| 6,505,074 B2 | 1/2003 | Boveja et al. | |
| 6,505,077 B1 | 1/2003 | Kast et al. | |
| 6,510,347 B2 | 1/2003 | Borkan | |
| 6,516,227 B1 | 2/2003 | Meadows et al. | |
| 6,535,766 B1 | 3/2003 | Thompson et al. | |
| 6,542,776 B1 | 4/2003 | Gordon et al. | |
| 6,553,263 B1 | 4/2003 | Meadows et al. | |
| 6,574,510 B2 | 6/2003 | Von Arx et al. | |
| 6,580,947 B1 | 6/2003 | Thompson | |
| 6,591,137 B1 | 7/2003 | Fischell et al. | |
| 6,597,954 B1 | 7/2003 | Pless et al. | |
| 6,600,956 B2 | 7/2003 | Maschino et al. | |

| | | |
|---|---|---|
| 6,607,500 B2 | 8/2003 | DaSilva et al. |
| 6,613,953 B1 | 9/2003 | Altura |
| 6,622,037 B2 | 9/2003 | Kasano |
| 6,622,048 B1 | 9/2003 | Mann et al. |
| 6,641,533 B2 | 11/2003 | Causey et al. |
| 6,643,552 B2 | 11/2003 | Edell et al. |
| 6,650,943 B1 | 11/2003 | Whitehurst et al. |
| 6,652,449 B1 | 11/2003 | Gross et al. |
| 6,658,300 B2 | 12/2003 | Gorari et al. |
| 6,660,265 B1 | 12/2003 | Chen |
| 6,672,895 B2 | 1/2004 | Scheiner |
| 6,684,109 B1 | 1/2004 | Osypka |
| 6,687,543 B1 | 2/2004 | Isaac |
| 6,701,188 B2 | 3/2004 | Stroebel et al. |
| 6,721,602 B2 | 4/2004 | Engmark et al. |
| 6,735,474 B1 | 5/2004 | Loeb et al. |
| 6,735,475 B1 | 5/2004 | Whitehurst et al. |
| 6,754,538 B2 | 6/2004 | Linberg |
| 6,775,715 B2 | 8/2004 | Spitaels |
| 6,804,558 B2 | 10/2004 | Haller et al. |
| 6,836,684 B1 | 12/2004 | Rijkhoff et al. |
| 6,836,685 B1 | 12/2004 | Fitz |
| 6,845,271 B2 | 1/2005 | Fang et al. |
| 6,850,803 B1 * | 2/2005 | Jimenez et al. ............ 607/61 |
| 6,855,410 B2 | 2/2005 | Buckley |
| 6,856,506 B2 | 2/2005 | Doherty |
| 6,859,364 B2 | 2/2005 | Yuasa et al. |
| 6,862,480 B2 | 3/2005 | Cohen et al. |
| 6,868,288 B2 | 3/2005 | Thompson |
| 6,891,353 B2 | 5/2005 | Tsukamoto |
| 6,895,280 B2 | 5/2005 | Meadows et al. |
| 6,904,324 B2 | 6/2005 | Bishay |
| 6,907,293 B2 | 6/2005 | Grill et al. |
| 6,907,295 B2 | 6/2005 | Gross et al. |
| 6,920,359 B2 | 7/2005 | Meadows et al. |
| 6,925,330 B2 | 8/2005 | Kleine |
| 6,928,320 B2 | 8/2005 | King |
| 6,937,894 B1 | 8/2005 | Isaac et al. |
| 6,941,171 B2 | 9/2005 | Mann et al. |
| 6,963,780 B2 | 11/2005 | Ruben et al. |
| 6,974,411 B2 | 12/2005 | Belson |
| 6,985,773 B2 | 1/2006 | Von Arx |
| 6,990,376 B2 | 1/2006 | Tanagho |
| 6,993,393 B2 | 1/2006 | Von Arx et al. |
| 6,999,819 B2 | 2/2006 | Swoyer et al. |
| 7,031,768 B2 | 4/2006 | Anderson et al. |
| 7,047,078 B2 | 5/2006 | Boggs, II et al. |
| 7,078,359 B2 | 7/2006 | Stepanian et al. |
| 7,101,607 B2 | 9/2006 | Mollendorf |
| 7,103,923 B2 | 9/2006 | Picotte |
| 7,118,801 B2 | 10/2006 | Ristic-Lehmann |
| 7,136,695 B2 | 11/2006 | Pless |
| 7,167,756 B1 | 1/2007 | Torgerson et al. |
| 7,177,690 B2 | 2/2007 | Woods et al. |
| 7,177,698 B2 | 2/2007 | Klosterman |
| 7,187,968 B2 | 3/2007 | Wolf |
| 7,187,983 B2 | 3/2007 | Dahlberg et al. |
| 7,191,012 B2 | 3/2007 | Boveja |
| 7,198,603 B2 | 4/2007 | Penner et al. |
| 7,225,032 B2 | 5/2007 | Schmeling et al. |
| 7,239,918 B2 | 7/2007 | Strother et al. |
| 7,254,448 B2 | 8/2007 | Almendinger et al. |
| 7,269,457 B2 | 9/2007 | Shafer et al. |
| 7,280,872 B1 | 10/2007 | Mosesov et al. |
| 7,283,867 B2 * | 10/2007 | Strother et al. ............ 600/546 |
| 7,317,947 B2 | 1/2008 | Wahlstrand |
| 7,328,068 B2 | 2/2008 | Spinelli et al. |
| 7,342,793 B2 | 3/2008 | Ristic-Lehmann |
| 7,343,202 B2 | 3/2008 | Mrva et al. |
| 7,369,897 B2 | 5/2008 | Boveja |
| 7,376,467 B2 | 5/2008 | Thrope |
| 7,437,193 B2 | 10/2008 | Parramon et al. |
| 7,443,057 B2 | 10/2008 | Nunally |
| 7,475,245 B1 | 1/2009 | Healy et al. |
| 7,499,758 B2 | 3/2009 | Cates |
| 7,565,198 B2 | 7/2009 | Bennett |
| 7,813,809 B2 * | 10/2010 | Strother et al. ............ 607/60 |
| 2001/0022719 A1 | 9/2001 | Armitage |
| 2002/0007198 A1 | 1/2002 | Haupert et al. |
| 2002/0019652 A1 | 2/2002 | DaSalva et al. |
| 2002/0055779 A1 | 5/2002 | Andrews |
| 2002/0077572 A1 | 6/2002 | Fang et al. |
| 2002/0109621 A1 | 8/2002 | Khair et al. |
| 2002/0161403 A1 | 10/2002 | Meadows et al. |
| 2002/0164474 A1 | 11/2002 | Buckley |
| 2003/0004434 A1 | 1/2003 | Greco et al. |
| 2003/0018365 A1 | 1/2003 | Loeb |
| 2003/0065368 A1 | 4/2003 | VanDerHoeven |
| 2003/0074030 A1 | 4/2003 | Leyde et al. |
| 2003/0078633 A1 | 4/2003 | Firlik et al. |
| 2003/0100930 A1 | 5/2003 | Cohen et al. |
| 2003/0114897 A1 | 6/2003 | Von Arx et al. |
| 2003/0114905 A1 | 6/2003 | Kuzma |
| 2003/0120259 A1 | 6/2003 | Mickley |
| 2003/0139783 A1 | 7/2003 | Kilgore et al. |
| 2003/0220673 A1 | 11/2003 | Snell |
| 2004/0030360 A1 | 2/2004 | Eini et al. |
| 2004/0059392 A1 * | 3/2004 | Parramon et al. ............ 607/36 |
| 2004/0082977 A1 * | 4/2004 | Engmark et al. ............ 607/36 |
| 2004/0088024 A1 | 5/2004 | Firlik et al. |
| 2004/0093093 A1 | 5/2004 | Andrews |
| 2004/0098068 A1 | 5/2004 | Carbunaru et al. |
| 2004/0147886 A1 | 7/2004 | Bonni |
| 2004/0150963 A1 | 8/2004 | Holmberg |
| 2004/0204744 A1 | 10/2004 | Penner et al. |
| 2004/0209061 A1 | 10/2004 | Farnworth |
| 2005/0004619 A1 | 1/2005 | Wahlstrand et al. |
| 2005/0038491 A1 | 2/2005 | Haack |
| 2005/0055063 A1 | 3/2005 | Loeb et al. |
| 2005/0080463 A1 | 4/2005 | Stahmann |
| 2005/0090756 A1 | 4/2005 | Wolf et al. |
| 2005/0107841 A1 | 5/2005 | Meadows et al. |
| 2005/0131493 A1 | 6/2005 | Boveja et al. |
| 2005/0143787 A1 | 6/2005 | Boveja et al. |
| 2005/0149146 A1 | 7/2005 | Boveja et al. |
| 2005/0175799 A1 | 8/2005 | Farnworth |
| 2005/0192526 A1 | 9/2005 | Biggs et al. |
| 2005/0278000 A1 | 12/2005 | Strother |
| 2006/0004421 A1 | 1/2006 | Bennett et al. |
| 2006/0025829 A1 | 2/2006 | Armstrong et al. |
| 2006/0033720 A1 | 2/2006 | Robbins |
| 2006/0035054 A1 | 2/2006 | Stepanian et al. |
| 2006/0100673 A1 | 5/2006 | Koinzer |
| 2006/0122660 A1 | 6/2006 | Boveja et al. |
| 2006/0149345 A1 | 7/2006 | Boggs, II et al. |
| 2006/0173507 A1 | 8/2006 | Mrva |
| 2006/0184208 A1 | 8/2006 | Boggs et al. |
| 2006/0195153 A1 | 8/2006 | DiUbaldi et al. |
| 2006/0271112 A1 | 11/2006 | Martinson et al. |
| 2007/0060967 A1 | 3/2007 | Strother |
| 2007/0060980 A1 | 3/2007 | Strother et al. |
| 2007/0100411 A1 | 5/2007 | Bonde |
| 2007/0123952 A1 | 5/2007 | Strother |
| 2007/0239224 A1 | 10/2007 | Bennett et al. |
| 2008/0065167 A1 | 3/2008 | Boggs, II et al. |
| 2008/0071322 A1 | 3/2008 | Mrva et al. |
| 2008/0097564 A1 | 4/2008 | Lathrop |
| 2008/0132969 A1 | 6/2008 | Bennett et al. |

FOREIGN PATENT DOCUMENTS

| | | |
|---|---|---|
| EP | 1468648 | 10/2004 |
| EP | 1790304 | 5/2007 |
| WO | WO00/19939 | 4/2000 |
| WO | WO01/83029 | 11/2001 |
| WO | WO 01/83029 A1 * | 11/2001 |
| WO | WO03/092227 | 4/2003 |
| WO | WO2005/122727 | 12/2005 |
| WO | WO2006/055547 | 5/2006 |
| WO | WO2006/133445 | 12/2006 |
| WO | WO2008/054448 | 5/2008 |
| WO | WO2009/058984 | 5/2009 |

OTHER PUBLICATIONS

2005 Biocontrol Medical Article: "Lower Urinary Tract," Israel Nissenkorn and Peter R. DeJong, pp. 1253-1258.

Mar. 2002 Physician's Manual: Cyberonics Model 201 NeuroCybernetic Prosthesis (NCP) Programming Wand, pp. 1-18.

Aug. 2002 Physician's Manual: Cyberonics Models 100 and 101 NeuroCybernetic Prosthesis System, NCP Pulse Generator, pp. 1-92.
2005 Advanced Neuromodulation systems, Inc.; ANS Medical—Determining Chronic Pain Causes and Treatments Website: http://www.ans-medical.com/medicalprofessional/physician/rechargeablejpgsystems.cfm.
2005 Cyberonics VNS Therapy website: http://www.vnstherapy.com/epilspsy/hcp/forsurgeons/implantedcomponents.aspx.
Final Office Action dated Oct. 13, 2011 for U.S. Appl. No. 12/825,089, (11 pgs.).
Responsive Amendment dated Dec. 13, 2011 for U.S. Appl. No. 12/825,089, (14 pgs.).
2004 Advanced Bionics Corporation Patient System Handbook.
2004 Advanced Bionics Corporation Physician Implant Manual.
2004 Advanced Bionics Corporation Summary of Safety and Effectiveness, pp. 1-18.
2005 Advanced Neuromodulation Systems, Inc.; ANS Medical—Determining Chronic Pain Causes and Treatments; website: www.ans-medical.com/medicalprofessional/physician/rechargeableipgsystems.cfm.
2005 Cyberonics VNS Therapy Website: www.vnstherapy.com/epilepsy/hcp/forsurgeons/implantedcomponents.aspx.
A Breakthrough in Advanced Materials, Aspen Aerogels, 2003 Inc. (1 pg) www.aerogels.com, 2003.
Aug. 2002 Physician's Manual; Cyberonics Models 100 and 101 NeuroCybernetic Prosthesis System, NCP Pulse Generator, pp. 1-92.
Bemelmans, Bart L.H., et al., "Neuromodulation by Implant for Treating Lower Urinary Tract Symptoms and Dysfunction," Eur. Urol. Aug. 1999 36(2): 81-91.
Bower, W.F., et al., "A Urodynamic Study of Surface Neuromodulation versus Sham in Detrusor Instability and Sensory Urgency", J. Urology 1998; 160: 2133-2136.
Brindley, G., et al., "Sacral Anterior Root Stimulators for Bladder Control in Paraplegia", Paraplegia 1982; 20(6):365-381.
Caldwell, C. (1971) Multielectrode Electrical Stimulation of Nerve, in Development of Orthotic Systems using Functional Electrical Stimulation and Myoelectric Control, Final Report Project #19-P-58391-F-01, University of Lublinana, Faculty of Electrical Engineering, Lubjiana, Yugoslavia.
Corbett, Scott S., http://crisp.cit.nih.gov/ Abstract, High-Density Liquid Crystal Polymer Cochlear Electrodes, downloaded Sep. 18, 2006.
Craggs, M., and McFarlane, J.P., "Neuromodulation of the Lower Urinary Tract," Experimental Physiology, 84, 149-160 1999.
Crampon et al., "Nerve Cuff Electrode with Shape Memory Alloy Armature: Design and Fabrication", *Bio-Medical Materials and Engineering* 12 (2002) 397-410.
Craggs, M., et al., "Aberrant reflexes and function of the pelvic organs following spinal cord injury in man", Autonomic Neuroscience: Basic & Clinical, 126-127 (2006), 355-370.
Crampon et al., "New Easy to Install Nerve Cuff Electrode Using Shape Memory Alloy Armature", *Artificial Organs*, 23(5):392-395, 1999.
Dalmose, A.L., et al., "Conditional Stimulation of the Dorsal Penile/Clitoral Nerve", Neurourol Urodyn 2003; 22(2):130-137.
Edell, David J., PhD, Boston Healthcare Research Device, Feb. 15, 2006.
Fossberg, E., et al. "Maximal Electrical Stimulation in the Treatment of Unstable Detrusor and Urge Incontinence", Eur Urol 1990; 18:120-123.
Grill, et al., "Emerging clinical applications of electrical stimulation: opportunities for restoration of function", Journal of Rehabilitation Research and Development, vol. 38, No. 6, Nov./Dec. 2001.
Grill, W. M., Mortimer, J.T., (1996) Quantification of recruitment properties of multiple contact cuff electrodes, IEEE Transactions on Rehabilitation Engineering 4(2):49-62.
Grill, W.M., (2001) "Selective Activation of the Nervous System for Motor System Neural Prosthesis" in Intelligent Systems and Technologies in Rehabilitation Engineering, H-N.L. Teodorescu, L. C. Jain, Eds., CRC Press, pp. 211-241.
Gustafson, K., et al. "A Urethral Afferent Mediated Excitatory Bladder Reflex Exists in Humans", Neurosci Lett 2004: 360(1-2):9-12.

Gustafson, K., et al., "A Catheter Based Method to Activate Urethral Sensory Nerve Fibers", J Urol 2003: 170(1):126-129.
Jezernik, S., "Electrical Stimulation for the Treatment of Bladder Dysfunction: Current Status and Future Possibilities", Neurol. Res. 2002: 24:413-30.
Jezernik, S., et al., "Detection and inhibition of hyper-reflexia-like bladder contractions in the cat by sacral nerve root recording and electrical stimulation," Neurourology and Urodynamics, 20(2), 215-230 (2001).
Jiang, C., et al., "Prolonged Increase in Micturition Threshold Volume by Anogenital Afferent Stimulation in the Rat", Br J. Urol. 1998: 82(3):398-403.
Jiang, C-H., et al., "Prolonged enhancement of the micturition reflex in the cat by repetitive stimulation of bladder afferents," Journal of Physiology, 517.2 599-605 (1999).
Juenemann, K., et al., Clinical Significance of Sacral and Pudendal Nerve Anatomy:, J. Urol. 1988; 139(1):74-80.
Lee, Y.H., et al., "Self-Controlled dorsal penile nerve stimulation to inhibit bladder hyperreflexia in incomplete spinal injury: A case report," Arch Phys Med Rehabil., 83, 273-7 (2002).
Loeb et al., "Cuff Electrodes for Chronic Stimulation and Recording of Peripheral Nerve Activity", *Journal of Neuroscience Methods*, 64 (1996), 95-103.
Madersbacher, H., Urinary Urge and Reflex Incontinence:, Urologe A. 1991: 30(4): 215-222 (Abstract only, article in German).
Mar. 2002 Physician's Manual; Cyberonics Model 201 NeuroCybernetic Prosthesis (NCP) Programming Wand, pp. 1-18.
Mazieres, L., et al., "Bladder Parasympathetic Response to Electrical Stimulation of Urethral Afferents in the Cat", Neurol Urodynam 1997; 16:471-472.
Mazieres, L., et al., "The C Fibre Reflex of the Cat Urinary Bladder", J. Physiol 1998; 513 (Pt 2):531-541.
McNeal, D.R., (1974) Selective Stimulation, in Annual Reports of Progress, Rehabilitation Engineering Center, Ranchio Los Amigos Hospital, Downey, CA, pp. 24-25.
McNeal, D.R., Bowman, B.R., (1985) Selective activation of muscles using peripheral nerve electrodes. Med. And Biol. Eng. And Comp., 23:249-253.
Modern Plastics Worldwide, Notables: 10 Waves of the Future by Modern Plastics Editorial Staff, Sample Molding in Progress: Sep. 1, 2005.
Nakamura, M., et al., "Bladder Inhibition by Penile Electrical Stimulation", Br J Urol 1984: 56:413-415.
Naples, et al., "A Spiral Nerve Cuff Electrode for Peripheral Nerve Stimulation", *IEEE Transactions on Biomedical Engineering*, vol. 35, No. 11, Nov. 1988.
NeuroControl Corp., NeuroControl StiM System brochure.
NeuroControl Corp., The NeuroControl StiM System, "World's First Miniturized Multi-Channel Programmable Neuromuscular Stimulator" brochure.
Nissenkorn, Israel, and De Jong, Peter R., 2005 Biocontrol Medical Article: "Lower Urinary Tract," pp. 1253-1258.
Nov. 21, 2001 Advanced Neuromodulation Systems, Inc. (ANS) Summary of Safety and Effectiveness Data, pp. 1-17.
Oct. 2001 Advanced Neuromodulation Systems, Inc., ANS Genesis Neurostimulation System Programmer User's Guide.
Oliver, S., et al., "Measuring the Sensations of Urge and Bladder Filling During Cystometry in Urge Incontinence and the Effects of Neuromodulation", Neurourol Urodyn 2003: 22:7-16.
Previnaire, J.G., "Short-Term Effect of Pudendal Nerve Electrical Stimulation on Detrusor Hyperreflexia in Spinal Cord Injury Patients: Importance of Current Strength", Paraplegia 1996: 34:95-99.
Rijkhoff, N., et al., "Urinary Bladder Control by Electrical Stimulation: Review of Electrical Stimulation Techniques in Spinal Cord Injury", Neurourol Urodyn 1997; 16(1):39-53.
Riley, George A., PhD, www.flipchips.com, Advanced Packaging—Water Level Hermetic Cavity Packaging, originally published in Advanced Packaging Magazine, May 2004.
Riley, George A., PhD, www.flipchips.com, Tutorial 31—Jun. 2003, A survey of Water Level Hermetic Cavity Chip Scale Packages for RF Applications.

Romero et al., "Neural Morphological Effects of Long-Term Implantation of the Self-Sizing Spiral Cuff Nerve Electrode", *Medical & Biological Engineering & Computing*, 2001, vol. 39, pp. 90-100.

Sahin et al., "Spiral Nerve Cuff Electrode for Recordings of Respiratory Output", *The Spiral Nerve Cuff Electrode*, 1997 American Physiological Society, pp. 317-322.

Schmidt, R.A., "Applications of Neurostimulation in Urology", 1988; 7:585-92.

Spinelli, M., et al., "A New Minimally Invasive Procedure for Pudendal Nerve Stimulation to Treat Neurogenic Bladder: Description of the Method and Preliminary Data", Neurourol and Urodyn. 2005: 24:305-309.

Starbuck, D. L., Mortimer, J.T., Sheally, C.N., Reswick, J.B. (1966) An implantable electrodes system for nerve stimulation, Proc $19^{th}$ Ann. Conf. on Eng. In Med. And Biol. 8:38.

Starbuck, D.L. (1965) Myo-electric control of paralyzed muscles. IEEE Transactions on Biomedical Engineering 12(3):169-172, Jul.-Oct.

Sundin, T., et al., "Detrusor inhibition induced from mechanical stimulation of the anal region and from electrical stimulation of pudendal nerve afferents," Investigative Urology, 5, 374-8 (1974).

Sweeney, et al., "A Nerve Cuff Technique for Selective Excitation of Peripheral Nerve Trunk Regions", *IEEE Transactions on Biomedical Engineering*, vol. 37, No. 7, 706-715, Jul. 1990.

Talaat, M., "Afferent Impulses in the Nerves Supplying the Urinary Bladder", Journal of Physiology 1937: 89-1-13.

Tanagho, E.A., et al. "Electrical Stimulation in the Clinical Management of the Neurogenic Bladder", J. Urol. 1988; 140:1331-1339.

Tyler, et al., "Chronic Response of the Rat Sciatic Nerve to the Flat Interface Nerve Electrode", *Annals of Biomedical Engineering*, vol. 31, pp. 633-642, 2003.

Veraart, C., Grill, W.M., Mortimer, J.T., (1993) Selective control of muscle activation with a multipolar nerve cuff electrode, IEEE Trans. Biomed. Engineering 40:640-653.

Vodusek, D.B., et al. "Detrusor Inhibition Induced by Stimulation of Pudendal Nerve Afferents", Neuroul and Urodyn., 1986; 5:381-389.

Wheeler, et al., "Bladder inhibition by penile nerve stimulation in spinal cord injury patients", The Journal of Urology, 147(1), 100-3 (1992).

Wheeler, et al., "Management of Incontinent SCI patients with Penile Stimulation; Preliminary Results," J. Am. Paraplegia Soc. Apr. 1994: 17(2):55-9.

www.devicelink.com, MPMN, May 2004, Liquid-Crystal Polymer Meets the Challenges of RF Power Packaging; The plastic air-cavity packages are hermetically sealed using a proprietary process, Susan Wallace.

www.foster-miller.com, Project Examples, Packaging for Implantable Electronics, Foster-Miller, Inc. Feb 15, 2006.

www.machinedesign.texterity.com, Vacuum-Formed Films for Fit and Function, High-Performance Films can Replace Injection-Molded Plastics when Space is at a Premium, David Midgley, Welch Fluorocarbon Inc., Dover, NH Oct. 7, 2004.

Yang, C., et al., "Peripheral Distribution of the Human Dorsal Nerve of the Penis", J. Urol 1998; 159(6):1912-6, discussion 1916.

PCT Search Report and Written Opinion dated Feb. 2, 2009 for PCT/US08/081762.

Reply to Written Opinion dated Nov. 13, 2008 for PCT/US07/014396.

Notification of Transmission of IPRP dated Jun. 26, 2009 for PCT/US07/014396.

Notification of Transmittal of the International Search Report and Written Opinion dated Jul. 18, 2008 for PCT/US08/002540.

MCP73841/2/3/4 Datasheet, "Advanced Single or Dual Cell Lithium-Ion/Lithium-Polymer Charge Management Controllers," Microchip Technology Inc., 2004 (24 pgs.).

Response to Communication dated May 10, 2011 for European Application No. 07777090.7 (2029219) filed Nov. 21, 2011, (37 pgs.).

Office Action dated Dec. 14, 2011 for U.S. Appl. No. 11/712,379, (10 pgs.).

Responsive Amendment dated Mar. 14, 2012 for U.S. Appl. No. 11/712,379, (10 pgs.).

* cited by examiner

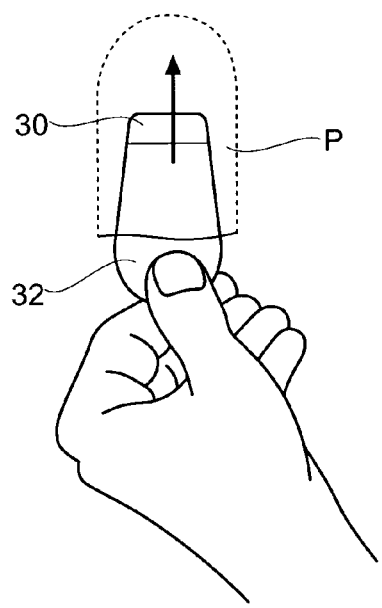
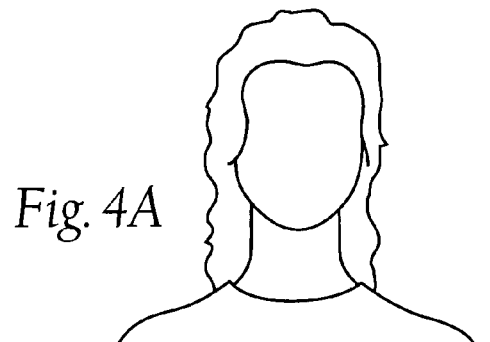
Fig. 3
Fig. 4A
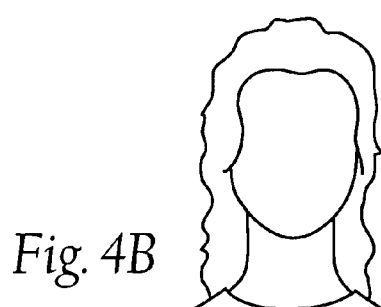
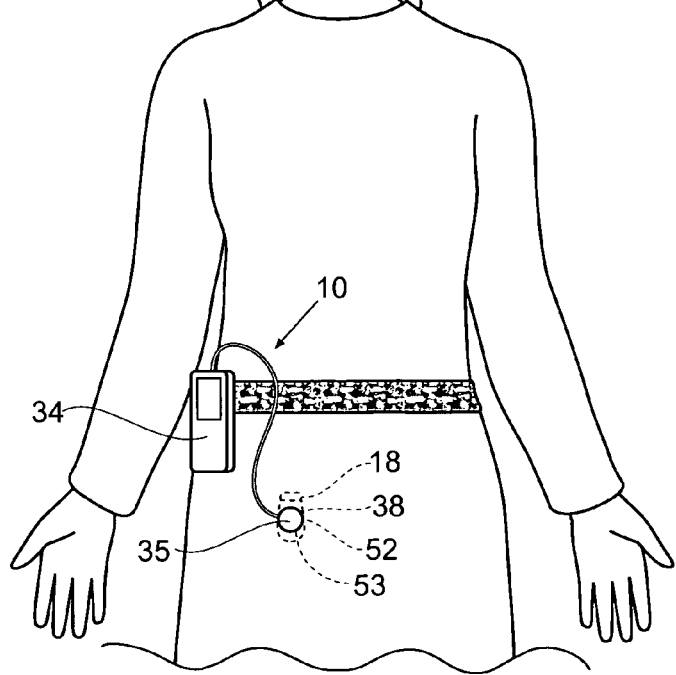
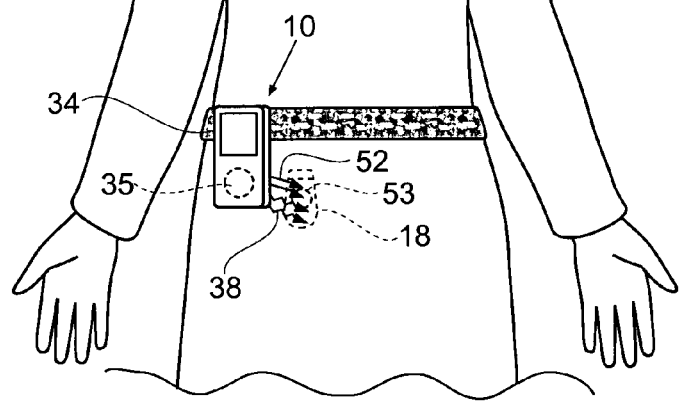
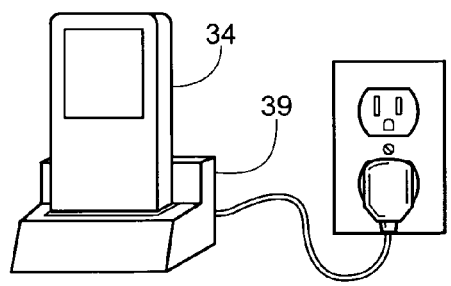
Fig. 4B
Fig. 4C

IMPLANTABLE SYSTEMS AND METHODS FOR ACQUISITION AND PROCESSING OF ELECTRICAL SIGNALS

RELATED APPLICATIONS

This application is a continuation application of U.S. Pat. No. 7,283,867, filed Jun. 10, 2005, which claims the benefit of U.S. Provisional Patent Application Ser. No. 60/578,742, filed Jun. 10, 2004, U.S. Provisional Patent Application Ser. No. 60/599,193, filed Aug. 5, 2004, and U.S. Provisional Patent Application Ser. No. 60/680,598, filed May 13, 2005, which are incorporated herein by reference.

FIELD OF INVENTION

This invention relates to devices, systems, and methods for acquisition and processing of electrical signals from tissues including central nervous system tissue, muscles, or nerves, or combinations thereof.

BACKGROUND OF THE INVENTION

The body generates electrical signals or impulses that produce contraction of tissue fibers. These electrical impulses are commonly referred to as myoelectric signals or MES. Myoelectric signals have frequencies ranging from a few hertz to about 300 Hz, and voltages ranging from approximately 10 microvolts to 1 millivolt. MES is most often associated with skeletal muscles that control voluntary movements, although MES also includes electrical signals within nerves or central nervous system tissue.

A variety of devices are available for acquisition and processing of myoelectric signals. These electrical signals are often used as instruction signals for control devices. As an example, acquisition and processing of myoelectric signals has been used to provide instruction signals to control systems that control mechanical movements of a prosthetic limb of its user. Or, the controller may direct other devices to provide electrical signals to muscles and/or nerves where the body is no longer able to generate an appropriate electronic signal.

These instruction signals are first generated by contraction of the user's own remaining muscles and are acquired from these muscles through a plurality of electrodes. The electrodes may be placed either on the external surface of the skin, or may be surgically implanted. A myoelectrically-controlled prosthesis uses these instruction signals (the electrical impulses) to operate a motor in a mechanical hand, work hook, or elbow, for example.

While existing devices, systems, and methods can provide adequate acquisition and processing of myoelectric signals, many limitations and issues still remain. For example, existing acquisition and processing systems are often external the body and therefore create a degree of nuisance and can degrade the quality of life of the user.

It is time that devices, systems, and methods for acquisition and processing of myoelectric signals address not only specific prosthetic or therapeutic objections, but also address the quality of life issues of prosthetic users.

SUMMARY OF THE INVENTION

The invention provides improved devices, systems, and methods for acquisition and processing of electric signals of tissues, including central nervous system tissue, muscles, or nerves, or muscles and nerves.

One aspect of the invention provides an electrical signal monitoring system. The monitoring system includes at least one electrically conductive surface adapted for implantation in a targeted tissue region, a lead electrically coupled to the electrically conductive surface, the lead adapted to be implanted in subcutaneous tissue, and an electrical signal processor electrically coupled to the lead.

The electrical signal processor is adapted to be implanted in subcutaneous tissue remote from the electrically conductive surface, and the electrical signal processor comprises a housing, the housing comprising a header and an electrically conductive case, electrical signal sensing circuitry positioned within the housing, the electrical signal sensing circuitry adapted to acquire and process electrical signals for therapeutic and/or functional restoration purposes, a rechargeable power source positioned within the housing to power the electrical signal processor, a receive coil positioned within the housing and adapted to receive a first radio frequency wireless telemetry, the first radio frequency wireless telemetry adapted to recharge the rechargeable power source, an antenna positioned within the housing and adapted to transmit and/or receive a second radio frequency wireless telemetry, the second radio frequency wireless telemetry adapted for communication with the electrical signal processor, and an electrical signal processor recharger, the electrical signal processor recharger adapted to transmit the first radio frequency wireless telemetry to the electrical signal processor to recharge the rechargeable power source, and the electrical signal processor recharger adapted to transmit and/or receive the second radio frequency wireless telemetry to and/or from the electrical signal processor for communication with the electrical signal processor.

In one embodiment, the electrical signal processor recharger is adapted to transmit the first radio frequency wireless telemetry to the electrical signal processor to recharge the rechargeable power source, and the electrical signal processor recharger is adapted to simultaneously transmit and/or receive the second radio frequency wireless telemetry to and/or from the electrical signal processor for communication with the electrical signal processor.

Another aspect of the invention provides an electrical signal processing system. The processing system comprises an electrical signal processor electrically coupled to a first lead, the first lead electrically coupled to at least one sensing electrode, the first lead and the sensing electrode are adapted to be implanted in subcutaneous tissue, and the electrical signal processor is adapted to be implanted in subcutaneous tissue remote from the sensing electrode.

The electrical signal processor comprises a housing, the housing comprising a header and an electrically conductive case, electrical signal sensing circuitry positioned within the housing, the electrical signal sensing circuitry adapted to acquire and process electrical signals for therapeutic and/or functional restoration purposes, a rechargeable power source positioned completely within the housing to power the electrical signal processor, a receive coil positioned completely within the housing and adapted for receiving a first radio frequency wireless telemetry, the first radio frequency wireless telemetry adapted for recharging the rechargeable power source.

A first antenna is positioned completely within the housing and adapted to transmit and/or receive a second radio frequency wireless telemetry, the second radio frequency wireless telemetry adapted for communication with the electrical signal processor.

An external recharger may be included, the recharger being adapted to transmit the first radio frequency wireless telemetry to the electrical signal processor to recharge the rechargeable power source, and the recharger being adapted to transmit and/or receive the second radio frequency wireless telemetry to and/or from the electrical signal processor for communication with the electrical signal processor.

In one aspect of the invention, an implantable pulse generator is included and is electrically coupled to a second lead, the second lead is electrically coupled to at least one stimulating electrode, the second lead and the stimulating electrode being adapted to be implanted in subcutaneous tissue, along with the implantable pulse generator being adapted to be implanted in subcutaneous tissue remote from the stimulating electrode.

The implantable pulse generator comprises electrical signal generating circuitry positioned within a pulse generator housing, the electrical signal generating circuitry adapted to generate electrical signals for therapeutic and/or functional restoration purposes, and a second antenna positioned completely within the pulse generator housing and adapted to transmit and/or receive the second radio frequency wireless telemetry to and/or from the electrical signal processor and/or recharger for communication with the electrical signal processor and/or recharger.

In one aspect of the invention, the recharger is adapted to transmit the first radio frequency wireless telemetry to the electrical signal processor to recharge the rechargeable power source, and the recharger is adapted to simultaneously transmit and/or receive the second radio frequency wireless telemetry to and/or from the electrical signal processor for communication with the electrical signal processor.

The second radio frequency wireless telemetry is functional as far as about two meters away from the electrical signal processor. The first radio frequency wireless telemetry may be at a different frequency than the second radio frequency wireless telemetry.

In yet another aspect of the invention, an electrical signal processor comprises a housing adapted to be implanted in subcutaneous tissue, the housing comprising a header and a hermetically sealed case, and electrical signal sensing circuitry positioned within the housing, the electrical signal sensing circuitry including suppression, amplification, and filtering circuitry adapted to acquire and process electrical signals for therapeutic and/or functional restoration purposes.

A rechargeable power source is positioned completely within the hermetically sealed case to power the electrical signal processor, and a receive coil is positioned completely within the hermetically sealed case and adapted to receive a first radio frequency wireless telemetry, the first radio frequency wireless telemetry adapted to recharge the rechargeable power source.

An antenna is positioned within the housing and adapted to transmit and/or receive a second radio frequency wireless telemetry while the receive coil is simultaneously receiving the first radio frequency wireless telemetry, and a spacing nest positioned completely within the hermetically sealed case, the spacing nest adapted to hold the rechargeable power source, the receive coil, and the electrical signal sensing circuitry in a predetermined relationship within the hermetically sealed case. The first radio frequency wireless telemetry may be at a lower frequency than the second radio frequency wireless telemetry.

The electrical signal sensing circuitry is adapted to provide stimulus pulses for the treatment of urinary incontinence, or fecal incontinence, or micturition/retention, or defecation/constipation, or restoration of sexual function, or pelvic floor muscle activity, or pelvic pain, or deep brain stimulation in the treatment of (i) Parkinson's disease; (ii) multiple sclerosis; (iii) essential tremor; (iv) depression; (v) eating disorders; (vi) epilepsy; (vii) minimally conscious state, or pain management by interfering with or blocking pain signals from reaching the brain in the treatment of (i) peripheral neuropathy; (ii) cancer, or obstructive sleep apnea.

In yet another aspect of the invention, a method is provided for monitoring electrical signals, the method comprising:

providing a lead including at least one electrically conductive surface, the lead adapted for implanting in subcutaneous tissue, providing an electrical signal processor, the electrical signal processor adapted for implanting in subcutaneous tissue remote from the electrically conductive surface, the electrical signal processor comprising a housing, the housing comprising a header and an electrically conductive case, electrical signal sensing circuitry positioned within the housing and electrically coupled to the lead, the electrical signal sensing circuitry adapted for acquiring and processing electrical signals for therapeutic and/or functional restoration purposes, a rechargeable power source positioned within the housing for powering the electrical signal processor, a receive coil positioned within the housing and adapted for receiving a first radio frequency wireless telemetry, the first radio frequency wireless telemetry adapted for recharging the rechargeable power source, and an antenna positioned completely within the housing and adapted for transmitting and/or receiving a second radio frequency wireless telemetry, the second radio frequency wireless telemetry adapted for communicating with the electrical signal processor, providing an electrical signal processor recharger, the electrical signal processor recharger adapted for transmitting the first radio frequency wireless telemetry to the electrical signal processor for recharging the rechargeable power source, and the electrical signal processor recharger adapted for transmitting and/or receiving the second radio frequency wireless telemetry to and/or from the electrical signal processor for communicating with the electrical signal processor, implanting the electrical signal processor in subcutaneous tissue, implanting the lead and electrode in subcutaneous tissue, the electrode being implanted remote from the electrical signal processor, coupling the lead to the electrical signal processor, operating the electrical signal processor to acquire and process electrical signals, operating the electrical signal processor recharger by transmitting the first radio frequency wireless telemetry to the electrical signal processor thereby recharging the rechargeable power source, and operating the electrical signal processor recharger by transmitting and/or receiving the second radio frequency wireless telemetry to and/or from the electrical signal processor thereby communicating with the electrical signal processor.

A further aspect of the invention provides a method comprising:

providing a housing adapted for implanting in subcutaneous tissue, the housing comprising a header and a hermetically sealed case, providing power management circuitry positioned completely within the housing, the power management circuitry comprising a rechargeable power source and a receive coil, the receive coil adapted for receiving a first radio frequency wireless telemetry from an external device, the first radio frequency wireless telemetry adapted for recharging the rechargeable power source, providing wireless telemetry circuitry positioned completely within the housing, the wireless telemetry circuitry comprising an antenna, the wireless telemetry circuitry adapted for transmitting and/or receiving a second radio frequency wireless telemetry to and/or from the external device, implanting the housing in subcutaneous tissue, transmitting the first radio frequency wireless telemetry from the external device to the receive coil for recharging the rechargeable battery, transmitting and/or receiving the second radio frequency wireless telemetry to and/or from the external device while the receive coil is receiving the first radio frequency wireless telemetry from the external device, and instructing the external device using the second radio frequency wireless telemetry to adjust a magnitude of the first radio frequency wireless telemetry to affect the recharging of the rechargeable power source.

The method may further comprise transmitting the second radio frequency wireless telemetry from the wireless telemetry circuitry for instructing a user of the external device to alter the position of the external device in relationship to the receive coil to affect the recharging of the rechargeable power source.

The method may also further comprise transmitting and/or receiving the second radio frequency wireless telemetry to and/or from the external device while the receive coil is simultaneously receiving the first radio frequency wireless telemetry from the external device.

In one embodiment, the power management circuitry comprises at least three power management operating modes including an active and charging mode, an active mode, and a dormant mode.

One aspect of the invention provides an implantable assembly sized and configured to acquire and process myoelectric signals of central nervous system tissue, muscles, or nerves, or muscles and nerves. The implantable assembly includes an implantable myoelectric signal (MES) processor attached to at least one lead and one electrode. The MES processor is implanted subcutaneously in tissue, preferably in a subcutaneous pocket located remote from the electrode. The electrode is implanted in electrical conductive contact (i.e., the electrode proximity to the tissue allows the electrode to sense the current flow through the tissue/nerve) with at least one functional grouping of neural tissue, muscle, or at least one nerve, or at least one muscle and nerve. The lead is tunneled subcutaneously in order to electrically connect the MES processor to the electrode.

Another aspect of the invention provides improved assemblies, systems, and methods for providing a universal device which can be used for acquisition and processing of myoelectric signals from muscle and/or nervous tissue for therapeutic (treatment) or prosthetic restoration purposes. Most of the components of the MES processor are desirably sized and configured so that they can accommodate several different indications, with no or only minor change or modification.

Desirable technical features of the MES processor device include one or more of the following: a secondary power source and/or primary power source for improved service life, wireless telemetry allowing communications between the implanted MES processor and external equipment, amplification and filtering circuitry for the acquisition of MES from one or more recording electrodes, electromagnetic compatibility (EMC) and electrostatic discharge (ESD) suppression circuitry for protection from damage or disruption by ESD or common electromagnetic interference sources, a lead connection header to provide reliable and easy connection and replacement of the lead/electrode, one or more programmable microcontrollers for timing and control of the MES processor device functions, including but not limited to the digitization digital processing of the amplified and filtered MES signals, and power management circuitry for efficient recharging of the secondary power source and the distribution of appropriate voltages and currents to other circuitry, all of which are incorporated within a small composite case for improved quality of life and ease of implantation.

In one embodiment, the MES signal can be captured by bipolar electrode pairs placed near the muscle group whose activity is to be monitored. In this arrangement, it is desirable that the wireless telemetry link be usable for one or more of the following functions: (1) communicating the results of the MES processing to external control or prosthetic hardware, (2) setting processing algorithm constants and limits, (3) determining the charge status of the battery in the implanted MES processor, (4) changing (re-programming) that operating program of the MES processor; including the MES processing/compression algorithm implemented by the implant, and (5) communicating with an externally mounted charger to allow the regulation of the strength of RF magnetic field generated to optimize the recharging of the MES Processor.

Another aspect of the invention provides an MES processor capable of acquisition and processing of myoelectric signals of central nervous system tissue, muscles, or nerves, or muscles and nerves. The MES processor is sized and configured to be implanted subcutaneously in a tissue pocket using a minimally invasive surgical procedure. The MES processor comprises an electrically conductive case, and can include a header that carries a plug-in receptacle(s) for attachment of a lead(s) and an antenna for transmission and reception of wireless telemetry signals. Within the case is located a circuit that amplifies and filters the myoelectric signals from one or more channels (bipolar electrode pair), EMC/ESD suppression circuitry, a rechargeable battery, recharging circuitry, a wireless telemetry circuit, and a programmable microcontroller which carries embedded code.

Yet another aspect of the invention provides improved assemblies, systems, and methods for providing an MES processor having improved power management circuitry and operating modes for extended service life. The power management circuitry is generally responsible for recovery of power from an RF magnetic field applied externally over the MES processor, for charging and monitoring the rechargeable battery, and for the distribution of appropriate voltages and currents to other circuitry in the MES processor. The power management circuitry (through the use of logic and algorithms implemented by the microcontroller) desirably communicates with an MES processor charger outside the body through the wireless telemetry communications link. The efficient recharging of the secondary power source (rechargeable battery) is accomplished by adjusting the strength of the RF magnetic field generated by the externally mounted MES processor charger in response to the magnitude of the voltage recovered by the MES processor and the power demands of the MES processor's battery. The power management may include operating modes configured to operate the MES processor at its most efficient power consumption throughout the storage and operation of the MES processor. These modes selectively disable or shut down circuit functions that are not needed. The modes may include, but are not limited to Active and Charging, Active, and Dormant.

Yet another aspect of the invention provides improved assemblies, systems, and methods for providing an MES processor incorporating wireless telemetry. Wireless telemetry allows the MES processor to wirelessly interact with a clinician programmer, a clinician programmer derivative, a patient controller, and an MES processor charger, for example. The wireless telemetry allows a clinician to transmit operational parameters, regimes, and other setting to the MES processor before or after it has been implanted. The wireless telemetry also allows the clinician to retrieve information stored in the MES processor about the patient's usage of the MES processor and information about any modifications to the settings of the MES processor made by the patient. The wireless telemetry also allows the patient controller operated by the user to control the MES processor, both operational parameters and settings in the context of a therapeutic application, or the real-time stimulus commands in the case of a neural prosthetic application. In addition, the wireless telemetry allows the MES processor to communicate with the recharger (MES processor charger) during a battery recharge in order to adjust the recharging parameters if necessary, which provides for an efficient and effective recharge. In addition, the wireless telemetry allows the operating program of the MES processor, i.e., the embedded executable code which incorporates the algorithms and logic for the operation of the MES processor, to be installed or revised after the MES processor has been assembled, tested, sterilized, and perhaps implanted. This feature could be used to provide flexibility to the manufacturer in the factory and perhaps to a representative of the manufacturer in the clinical setting.

Yet another aspect of the invention provides improved assemblies, systems and methods for providing a clinician programmer incorporating technology based on industry-standard hand-held computing platforms. The clinician programmer allows the clinician or physician to set parameters in the MES processor relating to the treatment of the approved indication. The clinician programmer uses the wireless telemetry feature of the MES processor to bi-directionally communicate to the MES processor. In addition, additional features are contemplated based on the ability of the clinician programmer to interact with industry standard software and networks to provide a level of care that improves the quality of life of the patient and would otherwise be unavailable. Such features, using subsets of the clinician programmer software, might include the ability of the clinician or physician to remotely monitor and adjust parameters using the Internet or other known or future developed networking schemes. A clinician programmer derivative (which can be a feature incorporated into the MES Processor charger) would connect to the patient's computer in their home through an industry standard network such as the Universal Serial Bus (USB), where in turn an applet downloaded from the clinician's server would contain the necessary code to establish a reliable transport level connection between the MES processor and the clinician's client software, using the clinician programmer derivative as a bridge. Such a connection may also be established through separately installed software. The clinician or physician could then view relevant diagnostic information, such as the health of the unit or its current efficacy, and then direct the patient to take the appropriate action. Such a feature would save the clinician, the patient and the health care system substantial time and money by reducing the number of office visits during the life of the implant.

Other features of the clinician programmer, based on an industry standard platform, might include the ability to connect to the clinician's computer system in his or hers office. Such features may take advantage of the Conduit connection employed by Palm OS based devices. Such a connection then would transfer relevant patient data to the host computer or server for electronic processing and archiving. With a feature as described here, the clinician programmer then becomes an integral link in an electronic chain that provides better patient service by reducing the amount of paperwork that the physician's office needs to process on each office visit. It also improves the reliability of the service since it reduces the chance of mis-entered or mis-placed information, such as the record of the parameter setting adjusted during the visit.

Other features and advantages of the inventions are set forth in the following specification and attached drawings.

BRIEF DESCRIPTION OF THE DRAWINGS

FIG. 3 is a view showing how the geometry of the MES processor shown in FIGS. 2A and 2B aids in its implantation in a tissue pocket.

FIG. 4A is a view showing the MES processor shown in FIGS. 2A and 2B in association with a transcutaneous MES processor charger (battery recharger) including an integral charging coil which generates the RF magnetic field, and also showing the MES processor charger using wireless telemetry to communicate with the MES processor.

FIG. 4B is an anatomic view showing the transcutaneous MES processor charger (battery recharger) as shown in FIG. 4A, including a separate, cable coupled charging coil which generates the RF magnetic field, and also showing the MES processor charger using wireless telemetry to communicate with the MES processor.

FIG. 4C is a perspective view of the MES processor charger of the type shown in FIGS. 4A and 4B, with the charger shown docked on a recharge base with the charging base connected to the power mains.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DESCRIPTION OF THE PREFERRED EMBODIMENTS

The various aspects of the invention will be described in connection with acquisition and processing of myoelectric signals of central nervous system tissue, muscles, or nerves, or muscles and nerves for prosthetic or therapeutic purposes. That is because the features and advantages that arise due to the invention are well suited to this purpose. Still, it should be appreciated that the various aspects of the invention can be applied to achieve other objectives as well.

I. MES Processing Assembly

A. System Overview

Figure 1:
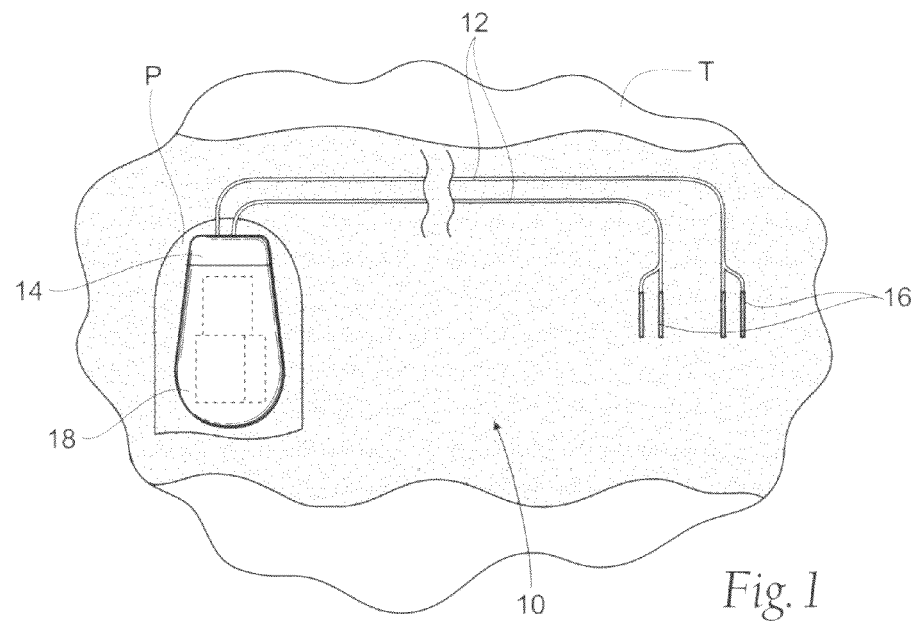
FIG. 1 is a view of a implantable assembly that acquires and processes electrical signals from central nervous system tissue, muscles and/or nerves inside the body using a general purpose MES processor.

FIG. 1 shows an assembly 10 for acquisition and processing of myoelectric signals from central nervous system tissue, nerve, or a muscle, or a nerve and a muscle for therapeutic (treatment) or functional restoration purposes. The assembly includes at least one implantable lead 12 coupled to an MES processor 18. The lead 12 and the MES processor 18 are shown implanted within a tissue region T of a human or animal body.

The distal end of the lead 12 includes one or more electrically conductive surfaces, which will in shorthand be called a recording electrode or electrode 16. The electrode 16 is desirably a bipolar electrode, and is implanted in electrical conductive contact with at least one functional grouping of neural tissue, muscle, or at least one nerve, or at least one muscle and nerve. The MES processor 18 includes a connection header 14 that desirably carries a plug-in receptacle for the lead 12. In this way, the lead 12 electrically connects the electrode 16 to the MES processor 18.

The MES processor 18 is sized and configured to be implanted subcutaneously in tissue, desirably in a subcutaneous pocket P, which can be remote from the electrode 16, as FIG. 1 shows. Desirably, the MES processor 18 is sized and configured to be implanted using a minimally invasive surgical procedure.

The surgical procedure may be completed in a number of steps. For example, once a local anesthesia is established, the electrode 16 is positioned at the target site. Next, a subcutaneous pocket P is made and sized to accept the MES processor 18. The pocket P is formed remote from the electrode 16. Having developed the subcutaneous pocket P for the MES processor 18, a subcutaneous tunnel is formed for connecting the lead 12 and electrode 16 to the MES processor 18. The lead 12 is routed through the subcutaneous tunnel to the pocket site P where the MES processor 18 is to be implanted. The lead 12 is then coupled to the MES processor 18, and both the lead 12 and MES processor 18 are placed into the subcutaneous pocket, which is sutured closed.

Figure 2A:
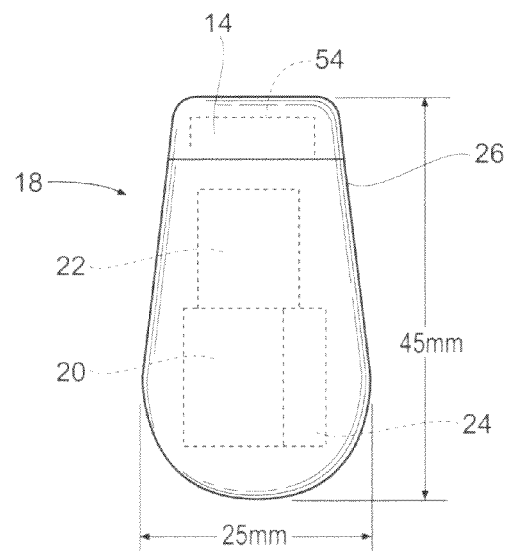
FIG. 2A is a front view of the general purpose MES processor shown in FIG. 1.
Figure 2B:
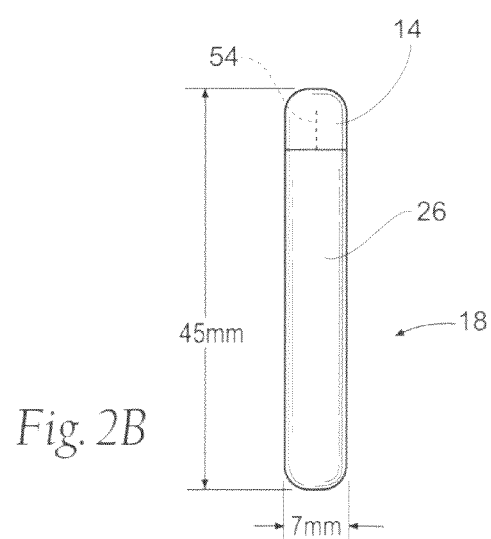
FIG. 2B is a side view of the general purpose MES processor shown in FIG. 2A.

As FIGS. 2A and 2B show, the MES processor 18 includes a circuit 20 that processes the electrical signals from the electrodes. An on-board, rechargeable battery 22 desirably provides the power for the circuitry of the MES processor. The MES processor 18 also desirably includes an on-board, programmable microcontroller 24, which carries embedded code. The code expresses pre-programmed rules or algorithms under which the myoelectric signal is processed; including the control of the analog amplification and filtering element of circuit 20.

According to its programmed rules, when switched on, the MES processor 18 processes the myoelectric signals sensed through the lead 12 and the electrode 16. These sensed electrical signals stem from neural activity of the central nervous system tissue, muscle, nerve, or both nerve and muscle tissue that lay in electrical conductive contact (i.e., within close proximity to the electrode surface where the electric field gradients from the nervous tissue are high) with the electrode 16, in order to provide a desirable control function; often under voluntary control of the patient/user. As previously discussed, control of a prosthetic limb is just one example of a prosthetic restoration result. Additional examples of desirable therapeutic (treatment) or functional restoration indications will be described in greater detail in section II.

The assembly 10 may also include additional operative components, such as but not limited to, a clinician programmer, a clinician programmer derivative, a patient controller, and an MES processor charger, each of which will be discussed later.

B. The MES Processor

Desirably, the size and configuration of the MES processor 18 makes possible its use as a general purpose or universal device (i.e., creating a platform technology), which can be used for many specific clinical indications requiring the acquisition and processing of electrical signals from central nervous system tissue, muscle and/or nervous tissue for therapeutic (treatment) or functional restoration purposes. Most of the components of the MES processor 18 are desirably sized and configured so that they can accommodate several different indications, without major change or modification. Examples of components that desirably remain unchanged for different indications include the case 26, the battery 22, the power management circuitry 40 for recharging the battery 22, the microcontroller 24, the wireless telemetry circuitry, much of the software (firmware) of the embedded code, EMC/ESD suppression circuitry, and the amplification, and filtering circuitry. Thus, a new indication may require only changes to the programming of the microcontroller 24. Most desirably, the particular code is remotely embedded in the microcontroller 24 after final assembly, packaging, sterilization, and perhaps implantation of the MES processor 18.

Certain components of the MES processor 18 may be expected to change as the indication changes; for example, due to differences in leads and electrodes, the connection header 14 and associated receptacle(s) for the lead may be configured differently for different indications. Other aspects of the circuit 20 may also be modified to accommodate a different indication; for example additional channels of MES processing.

In this way, the MES processor 18 is well suited for use for diverse indications. The MES processor 18 thereby accommodates coupling to a lead 12 and an electrode 16 implanted in diverse tissue regions, which are targeted depending upon the therapeutic (treatment) or functional restoration results desired. The MES processor 18 also accommodates coupling to a lead 12 and an electrode 16 having diverse forms and configurations, again depending upon the therapeutic or functional effects desired. For this reason, the MES processor can be considered to be general purpose or "universal."

1. Desirable Technical Features

The MES processor 18 can incorporate various technical features to enhance its universality.

a. Small, Composite Case

According to one desirable technical feature, the MES processor 18 can be sized small enough to be implanted (or replaced) with only local anesthesia. As FIGS. 2A and 2B show, the functional elements of the MES processor 18 (e.g., circuit 20, the microcontroller 24, the battery 22, and the connection header 14) are integrated into a small, composite case 26. As FIGS. 2A and 2B show, the case 26 defines a small cross section; e.g., (5 mm to 10 mm thick)×(30 mm to 40 mm wide)×(50 mm to 60 mm long), and an overall weight of approximately 20 to 25 grams. These dimensions make possible implantation of the case 26 with a small incision; i.e., suitable for minimally invasive implantation.

The case 26 of the MES processor 18 is desirably shaped with a smaller end 30 and a larger end 32. As FIG. 3 shows, this geometry allows the smaller end 30 of the case 26 to be placed into the skin pocket P first, with the larger end 32 being pushed in last.

Desirably, the case 26 for the MES processor 18 comprises a laser welded titanium material. This construction offers high reliability with a low manufacturing cost. The clam shell construction has two stamped or successively drawn titanium case halves that are laser welded around the circuit assembly and battery 22 with feed-thrus. Typically, a molded plastic spacing nest is used to hold the battery 22, the circuit 20, and perhaps a power recovery (receive) coil 53 together and secure them within the titanium case.

The MES processor 18 shown in FIGS. 2A and 2B includes a clam-shell case 26 having a thickness that is selected to provide adequate mechanical strength while balancing the greater power absorption and shielding effects to the low to medium frequency magnetic field used to transcutaneously recharge the MES processor Lithium Ion battery 22 with thicker case material (the competing factors are poor transformer action at low frequencies—due to the very low transfer impedances at low frequencies—and the high shielding losses at high frequencies). The selection of the thickness ensures that the titanium case allows adequate power coupling to recharge the secondary power source (described below) of the MES processor 18 at the target implant depth using a low frequency radio frequency (RF) magnetic field from an MES processor charger 34 mounted on the skin. Preferably, the MES processor 18 is implanted at a target implant depth of not less than five millimeters beneath the skin, and not more than fifteen millimeters beneath the skin, although this implant depth may change due to the particular application, or the implant depth may change over time based on physical conditions of the patient, for example.

b. Secondary Power Source

According to one desirable technical feature, the MES processor 18 desirably possesses an internal battery capacity sufficient to allow operation with recharging not more frequently than once per week for many or most clinical applications. The battery 22 of the MES processor 18 desirably can be recharged in less than approximately six hours with a recharging mechanism that allows the patient to sleep in bed or carry on most normal daily activities while recharging the battery 22 of the MES processor 18.

To achieve this feature, the battery 22 of the MES processor 18 desirably comprises a secondary (rechargeable) power source; most desirably a Lithium Ion battery 22. Given the average quiescent operating current (estimated at 8 µA plus 35 µA for a wireless telemetry receiver pulsing on twice every second) and a 250 µA budget for analog and digital processing (for 3 hours a day), a 1.0 Amp-hr primary cell battery can provide a service life of less than two years, which is too short to be clinically or commercially viable for this indication. Therefore, the MES processor 18 desirably incorporates a secondary battery 22 (a rechargeable battery), e.g., a Lithium Ion secondary battery that can be recharged transcutaneously. Given representative desirable stimulation parameters (which will be described later), a Lithium Ion secondary battery with a capacity of 30 mA-hr will operate for about two weeks. Lithium Ion implant grade batteries are available from a domestic supplier. A representative battery provides 35 mA-hr in a package configuration that is of appropriate size and shape to fit within the MES processor 18. The MES processor 18 could also incorporate a small primary battery to provide current to prevent self-discharge of the secondary battery 22 from dropping its voltage to the point of irreversible damage to the secondary battery.

The power for recharging the battery 22 of the MES processor 18 is provided through the application of a low frequency (e.g., 30 KHz to 300 KHz) RF magnetic field applied by a skin or clothing mounted recharger 34 placed over the MES processor (see FIGS. 4A and 4B). In one possible application, it is anticipated that the user would wear the recharger 34, including an internal magnetic coupling coil (charging coil) 35, over the MES processor 18 to recharge the MES processor 18 (see FIG. 4A). Alternatively, the recharger 34 might use a separate magnetic coupling coil (charging coil) 35 which is placed and/or secured on the skin or clothing over the MES processor 18 and connected by cable to the recharger 34 (circuitry and battery in a housing) that is worn on a belt or clipped to the clothing (see FIG. 4B).

The charging coil 35 preferably includes a predetermined construction, e.g., desirably 150 to 250 turns, and more desirably 200 turns of six strands of #36 enameled magnetic wire, or the like. Additionally, the charging coil mean diameter is in a range of about 40 millimeters to 60 millimeters, and desirably about 50 millimeters, although the diameter may vary. The thickness of the charging coil 35 as measured perpendicular to the mounting plane is to be significantly less than the diameter, e.g., two to five millimeters, so as to allow the coil to be embedded or laminated in a sheet to facilitate placement on or near the skin. Such a construction will allow for efficient power transfer and will allow the charging coil 35 to maintain a temperature below 41 degrees Celsius.

The recharger 34 preferably includes its own internal batteries which may be recharged from the power mains, for example. A charging base 39 may be included to provide for convenient docking and recharging of the system's operative components, including the recharger and the recharger's internal batteries (see FIG. 4C). The MES processor recharger 34 does not need to be plugged into the power mains while in use to recharge the MES processor.

Desirably, the MES processor 18 may be recharged while it is operating and will not increase in temperature by more than two degrees Celsius above the surrounding tissue during the recharging. It is desirable that the recharging of the battery 22 requires not more than six hours, and a recharging would be required between once per month to once per week depending upon the power requirements of the acquisition and processing activity.

The MES processor 18 desirably incorporates circuitry and/or programming to assure that the MES processor 18 will suspend MES acquisition and processing, and perhaps fallback to only very low rate telemetry, and eventually suspends all operations when the secondary battery 22 has discharged the majority of it capacity (i.e., only a safety margin charge remains). Once in this dormant mode, the MES processor can be restored to normal operation only by recharging as shown in FIGS. 4A and 4B.

c. Wireless Telemetry

According to one desirable technical feature, the system or assembly 10 includes an MES Processor 18, which desirably incorporates wireless telemetry (rather that an inductively coupled telemetry) for a variety of functions to be performed within arm's reach of the patient, the functions including receipt of programming and clinical parameters and settings from the clinician programmer 36, communicating usage history to the clinician programmer, providing user control of the MES processor 18, and for controlling the RF magnetic field generated by the MES processor charger 34. Each implantable MES processor 18 may also have a unique signature that limits communication to only the dedicated controllers (e.g., the matched Patient Controller, MES processor charger, or a clinician programmer configured for the MES processor 18 in question).

Figure 6:
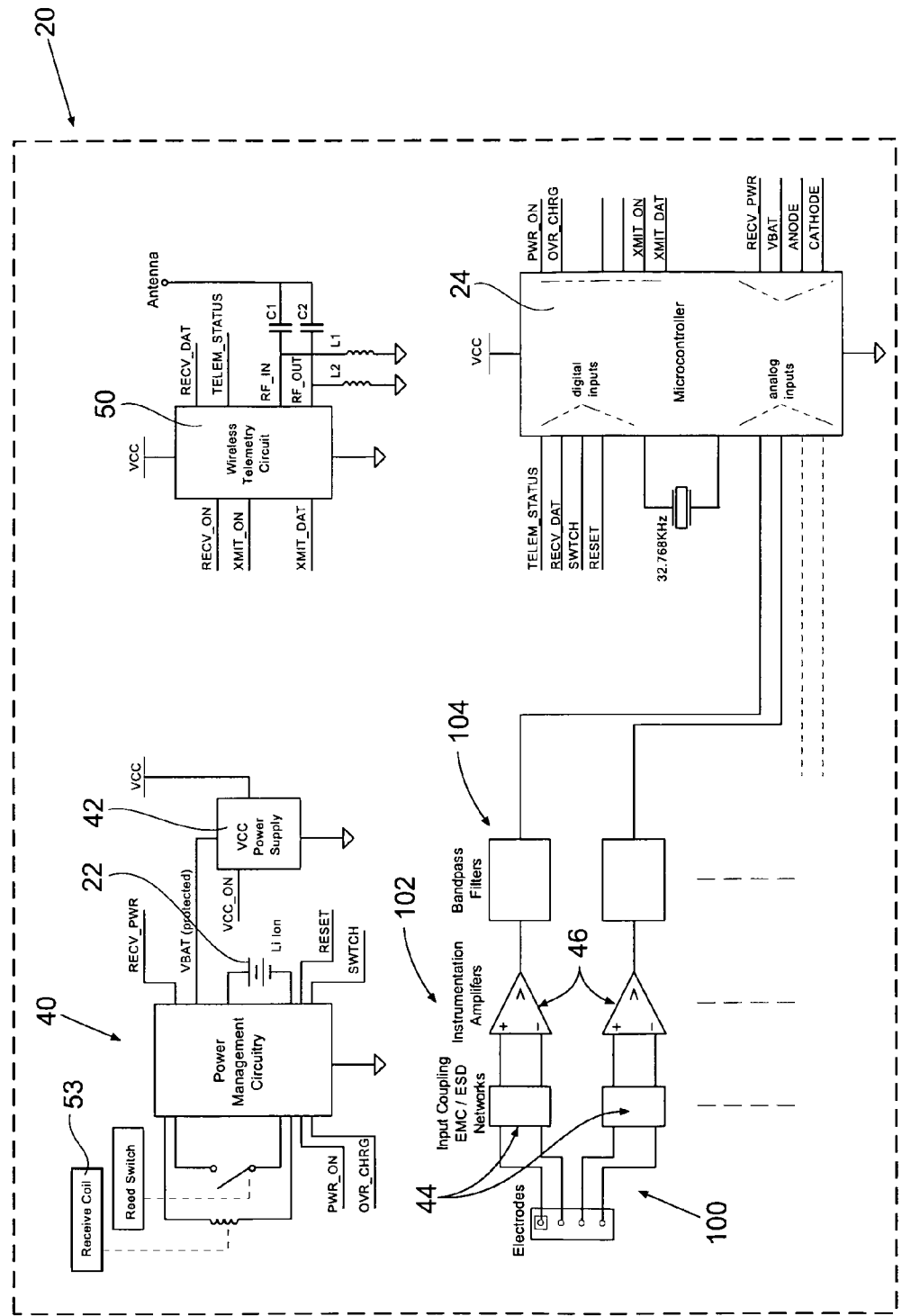
FIG. 6 is a block diagram of a circuit that the MES processor shown in FIGS. 2A and 2B can incorporate.
Figure 7:
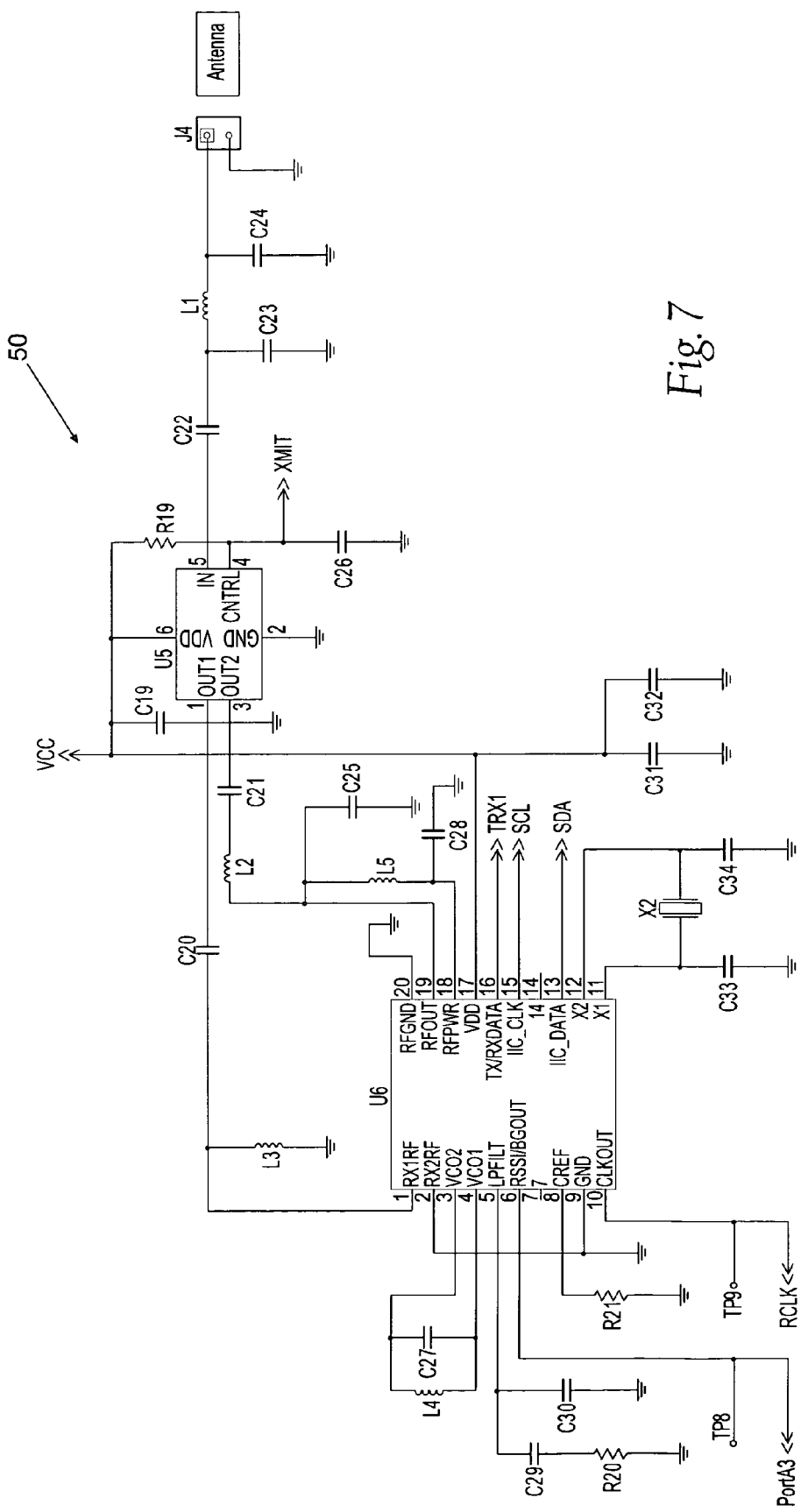
FIG. 7 is a circuit diagram showing a possible circuit for the wireless telemetry feature used with the MES processor shown in FIGS. 2A and 2B.

The MES processor 18 desirably incorporates wireless telemetry as an element of the MES processor circuit 20, a representative embodiment of which is shown in FIG. 6. A circuit diagram 50 showing a desired configuration for the wireless telemetry feature is shown in FIG. 7. It is to be appreciated that modifications to this circuit diagram configuration which produce the same or similar functions as described are within the scope of the invention.

Figure 5A:
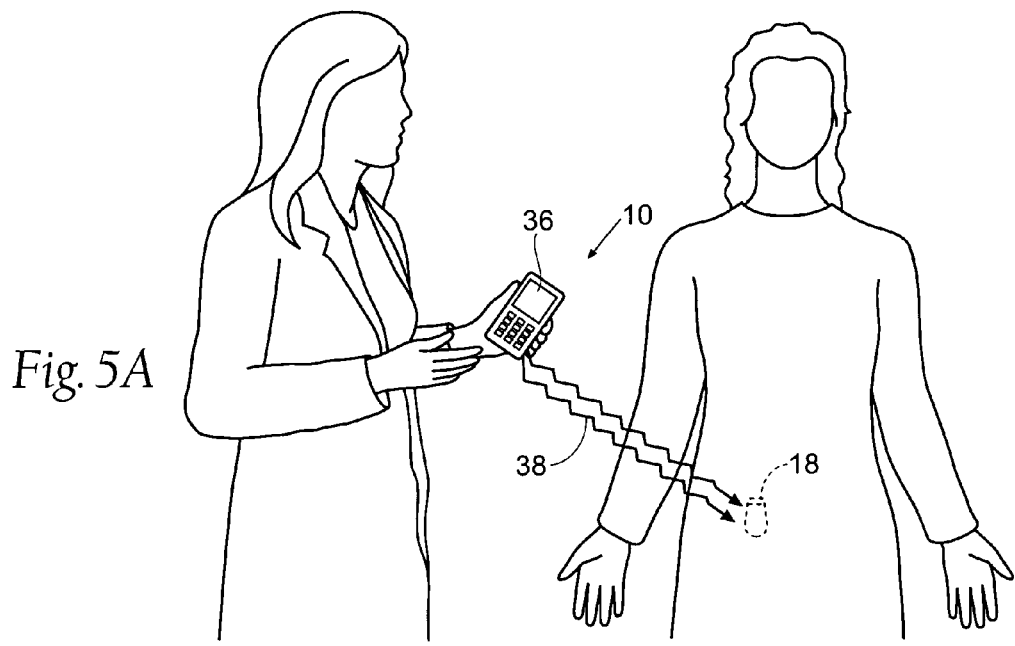
FIG. 5A is an anatomic view showing the MES processor shown in FIGS. 2A and 2B in association with an external programmer that relies upon wireless telemetry, and showing the programmer's capability of communicating with the MES processor up to an arm's length away from the MES processor.

As shown in FIG. 5A, the assembly 10 desirably includes a clinician programmer 36 that, through a wireless telemetry 38, transfers commands, data, and programs into the MES processor 18 and retrieves data out of the MES processor 18. In some configurations, the clinician programmer may communicate with more than one MES processor implanted in the same user. Additionally, the MES processor may be used as part of a system with implantable stimulators that use a compatible wireless telemetry system. Thus the communications between the MES Processor and the patient controller may also be monitored by the implantable stimulator(s) and form an neuroprosthetic system with minimal communications originating from the patient controller.

The clinician programmer 36 may incorporate a custom programmed general purpose digital device, e.g., a custom program, industry standard handheld computing platform or other personal digital assistant (PDA). The clinician programmer 36 can include an on-board microcontroller powered by a rechargeable battery. The rechargeable battery of the clinician programmer 36 may be recharged in the same or similar manner as described and shown for the recharger 34, i.e., docked on a charging base 39 (see FIG. 4C); or the custom electronics of the clinician programmer may receive power from the connected PDA.

Figure 5B:
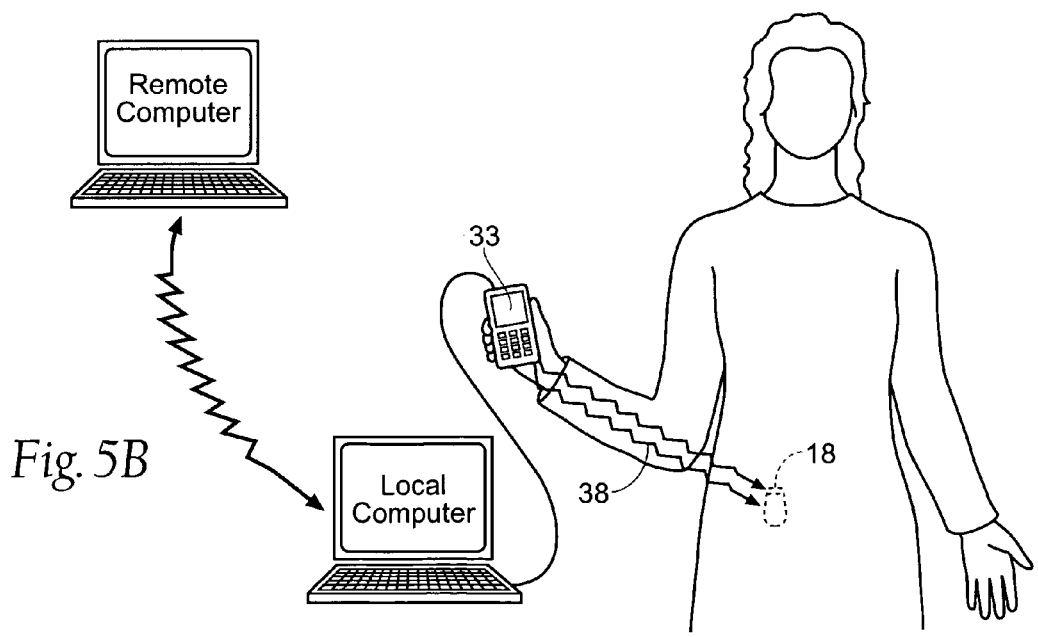
FIG. 5B is a system view of an MES processor system incorporating a clinician programmer derivative and showing the system's capability of communicating and transferring data over a network, including a remote network.

The microcontroller carries embedded code which may include pre-programmed rules or algorithms that allow a clinician to remotely download acquisition and processing parameters into the MES processor 18. The microcontroller of the clinician programmer 36 is also desirably able to interrogate the MES processor and upload usage data from the MES processor. FIG. 5A shows one possible application where the clinician is using the programmer 36 to interrogate the MES processor. FIG. 5B shows an alternative application where the clinician programmer, or a clinician programmer derivative 33 intended for remote programming applications and having the same or similar functionality as the clinician programmer, is used to interrogate the MES processor. As can be seen, the clinician programmer derivative 33 is connected to a local computer, allowing for remote interrogation via a local area network, wide area network, or Internet connection, for example. Such a clinician programmer derivative may be included as a feature of the MES processor charger.

Using subsets of the clinician programmer software, features of the clinician programmer 36 or clinician programmer derivative 33 might include the ability of the clinician or physician to remotely monitor and adjust parameters using the Internet or other known or future developed networking schemes. A clinician programmer derivative 33 would desirably connect to the patient's computer in their home through an industry standard network such as the Universal Serial Bus (USB), where in turn an applet downloaded from the clinician's server would contain the necessary code to establish a reliable transport level connection between the MES processor 18 and the clinician's client software, using the clinician programmer derivative 33 as a bridge. Such a connection may also be established through separately installed software. The clinician or physician could then view relevant diagnostic information, such as the health of the unit or its current efficacy, and then direct the patient to take the appropriate action. Such a feature would save the clinician, the patient and the health care system substantial time and money by reducing the number of office visits during the life of the implant.

Other features of the clinician programmer, based on an industry standard platform, might include the ability to connect to the clinician's computer system in his or hers office. Such features may take advantage of the Conduit connection employed by Palm OS® based devices. Such a connection then would transfer relevant patient data to the host computer or server for electronic processing and archiving. With a feature as described here, the clinician programmer then becomes an integral link in an electronic chain that provides better patient service by reducing the amount of paperwork that the physician's office needs to process on each office visit. It also improves the reliability of the service since it reduces the chance of mis-entered or mis-placed information, such as the record of the parameter setting adjusted during the visit.

With the use of a patient controller 37 (see FIG. 5C), the wireless link 38 allows a patient to control a limited range of parameters within the MES processor, such as operation modes/states, increase/decrease or optimize thresholds of MES activity associated with neuroprosthetic or therapeutic actions, or provide open or closed loop feedback from an external sensor or control source. The wireless telemetry 38 also desirably allows the user to interrogate the MES processor 18 as to the status of its internal battery 22. The full ranges within these parameters may be controlled, adjusted, and limited by a clinician, so the user may not be allowed the full range of possible adjustments.

Figure 5C:
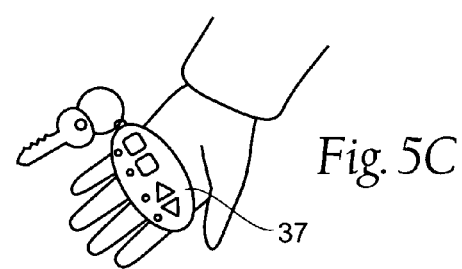
FIG. 5C is a perspective view of a patient controller that may be used with the MES processor shown in FIGS. 2A and 2B.

In one embodiment, the patient controller 37 is sized and configured to couple to a key chain, as seen in FIG. 5C. It is to be appreciated that the patient controller 37 may take on any convenient shape, such as a ring on a finger, or a watch on a wrist, or an attachment to a belt, for example. It may also be desirable to combine both the functions of the MES processor charger and the patient controller into a single external device.

The recharger 34 shown in FIGS. 4A and 4B may also use wireless telemetry to communicate with the MES processor 18, so as to adjust the magnitude of the magnetic field to allow optimal recharging of the MES processor battery 22 while minimizing unnecessary power consumption by the recharger and power dissipation in the MES processor (through circuit losses and/or through absorption by MES processor case and construction).

For example, the wireless telemetry may incorporate a suitable, low power wireless telemetry transceiver (radio) chip set that can operate in the MICS (Medical Implant Communications Service) band (402 MHz to 405 MHz) or other VHF/UHF low power, unlicensed bands. A wireless telemetry link not only makes the task of communicating with the MES processor 18 easier, but it also makes the link suitable for use in motor control applications where the user voluntarily produces muscle contractions that are senses by the MES processor, and in turn, the MES processor issues a request to the external controller to activate an implantable pulse generator to produce stimulus pulses which in turn produce muscle contractions to achieve a functional goal (e.g., to squeeze a prosthetic hand or to stimulate ankle flexion to aid in the gait of an individual after a stroke) without requiring a coil or other component taped or placed on the skin over the implanted implantable pulse generator.

Appropriate use of power management techniques is important to the effective use of wireless telemetry. Desirably, the MES processor is exclusively the communications slave, with all communications initiated by the external controller (the communications master). The receiver chip of the MES processor is OFF more than 99% of the time and is pulsed on periodically to search for a command from an external controller, including but not limited to the MES processor charger 34, the clinician programmer 36, and the patient controller 37. Communications protocols include appropriate check and message acknowledgment handshaking to assure the necessary accuracy and completeness of every message. Some operations (such as reprogramming or changing stimulus parameters) require rigorous message accuracy testing and acknowledgement. Other operations, such as a single user command value in a string of many consecutive values, might require less rigorous checking and a more loosely coupled acknowledgement.

The timing with which the MES processor enables its transceiver to search for RF telemetry from an external controller is precisely controlled (using a time base established by a quartz crystal) at a relatively low rate (e.g., twice per second; i.e., every 500 milliseconds). This allows the external controller to time when the MES processor responds to a command and then to synchronize its commands with when the MES processor will be listening for commands. This, in turn, allows commands issued within a short time (seconds to minutes) of the last command to be captured and acted upon without having to 'broadcast' an idle or pause signal for 500 milliseconds before actually issuing the command in order to know that the MES processor will have enabled its receiver and received the command. Similarly, the communications sequence is configured to have the external controller issue commands in synchronization with when the MES processor will be listening for a command. Similarly, the command set implemented is selected to minimize the number of messages necessary and the length of each message consistent with the appropriate level of error detection and message integrity monitoring. It is to be appreciated that the monitoring rate may vary faster or slower depending on the application; and may vary over time within a given application.

The input processing firmware allows the telemetry link to be idle except when myoelectric signal activity corresponds to a command or other important sequence. At that point the wireless telemetry can become active with a higher average data rate. In normal operation, the average latency between a MES event and the associated data on the telemetry link is about $\frac{1}{10}$ second. Depending on the application, the MES processor might fully implement a control algorithm and telemeter out the final result/command (for a prosthesis, neuroprosthesis, or therapeutic application); or it might partially process the MES signal(s) and telemeter out the intermediate result; or it might perform data compression and telemeter out the compressed MES data for processing by other devices.

In some applications, an external wireless accessory receives the wireless telemetry from the implanted MES processor and can provide a control signal to other appliances or recode and transmit new commands to a implantable pulse generator used as an FES neuroprostheses. In other applications, the implanted or external devices could directly monitor the data being telemetered from the MES processor. In other applications, the wireless interface device (which must be located within about two meters of the implanted device) could provide the received data to a general purpose computer (perhaps a Personal Digital Assistant (PDA)) through a USB serial port. The PDA (or other appliance) can implement simple or sophisticated control algorithms and then control the motor or therapeutic devices.

A suitable radio chip is used for the half duplex wireless communications, e.g., the AMIS-52100 (AMI Semiconductor; Pocatello, Id.). This transceiver chip is designed specifically for the MICS and its European counter-part the ULP-AMI (Ultra Low Power-Active Medical Implant) band. This chip set is optimized by micro-power operation with rapid start-up, and RF 'sniffing' circuitry.

d. MES Amplication and Filtering Circuitry

Figure 9:
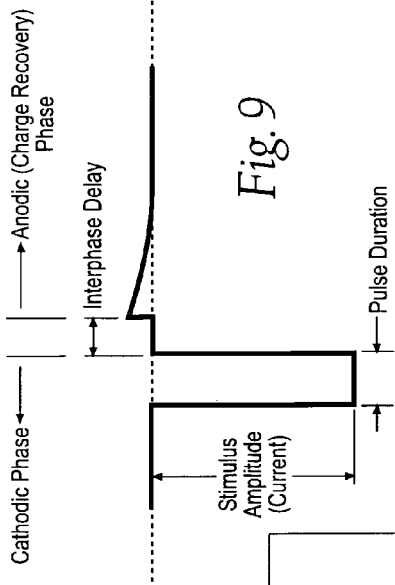
FIG. 9 is a graphical view of a typical myoelectric signal to be sensed by the MES processor while in use with the system shown in FIG. 1.

The MES processor circuit 20 desirably incorporates one or more independent myoelectric signal recording channels 100 (see FIG. 6) coupled to a recording electrode 16. FIG. 9 is a graphical view of a typical myoelectric signal to be sensed by the MES processor while in use with the system shown in FIG. 1.

Each channel 100 has an instrumentation amplifier 102 designed for minimizing the magnitude of signal artifacts. These artifacts could arise from conventional sources of MES interference (presence of externally generated 60 Hz electric or magnetic fields, presence of higher frequency (RF) electromagnetic fields associated with the external environment, changing forces or pressures on the tissue over the recording electrodes, etc.). The MES artifacts could also arise from the use of electrical stimulation near the MES processor or its electrodes and leads. Specifically, if the MES processor is being used as part of a neuroprosthetic system or as part of a therapeutic system that incorporates electrical stimulation of muscles in the same extremity (or body region) as the MES processor; such stimulus artifact is likely to contaminate the MES signal.

The central methods for minimizing these artifacts (all sources) desirably include one or more of the following features: (1) the instrumentation amplifier should maintain a high common mode rejection ratio throughout the frequency range of the artifact (note that the instrumentation amplifier should reject common mode signals at frequencies lower than the EMG signal); (2) the inputs to the instrumentation amplifier should be protected from damage by Electrostatic Discharge (ESD); (3) the inputs to the instrumentation amplifier should be filtered to reduce the harmful effects of radio frequency interference (RFI); (4) the coupling of the electrodes to the instrumentation amplifier should not excessively degrade the effective common mode rejection ratio (CMRR) of the instrumentation amplifier (which may be problematic at low frequencies); (5) the ESD protection and RFI filtering methods should not excessively degrade the effective CMRR of the instrumentation amplifier (especially problematic at low frequencies), and (6) the common mode voltage of the MES signal (available as an intermediate output of the instrumentation amplifier) is monitored by hardware and used to suspend MES processing during and immediately after very high artifact levels (typically stimulus artifact).

The output of each instrumentation amplifier (one per MES channel) is then bandpass filtered by a bandpass filter 104. The low band edge eliminates the DC content and frequencies where the artifact can be large and there is little EMG content. The high band edge corresponds to an anti-aliasing filtering before the signal is digitized. These bandpass filtered signals are then sampled (digitized) by the 12-bit analog to digital converter channels of the microcontroller 24.

Figure 8:
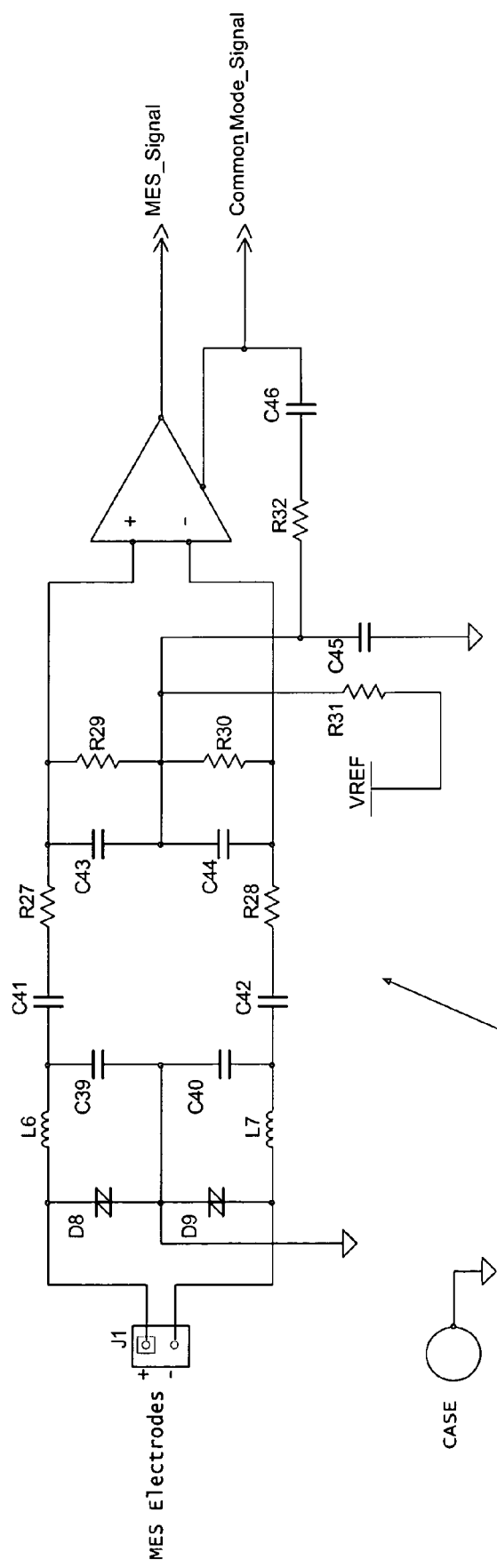
FIG. 8 is a circuit diagram showing a possible circuit for the amplification and filtering features used with the MES processor shown in FIGS. 2A and 2B. This circuit includes provisions for the EMC/ESD suppression features used with the MES processor shown in FIGS. 2A and 2B. This circuit may also include methods for the detection of stimulus artifacts and their subsequent suppression by processing software (firmware).

A representative signal processing circuitry of a given myoelectric signal recording channel 100 is shown in FIG. 8. As shown in FIG. 8, D8 and D9 are the transient suppressor diodes which clamp the voltage from the MES electrodes to ground (the case of the MES processor) in the event of large ESD or EMC disruptions; but these components have no current flow in normal operation (including during typical MES artifacts). L6-C39 and L7-C40 form RFI filters to attenuate RFI to circuit common. These parts might incorporate ferrite elements and may be designed for maximal efficiency in attenuating common-mode voltages. R27-C43 and R28-C44 form R-C filters that further attenuate RFI and higher audio frequency signal artifacts. These filters are returned to a common mode return node (junction of R29, C43, R30, C44, R31, C45, and R32) that has the DC voltage established by VREF, very high frequency signals attenuated, and for MES passband signals, is at the AC potential of the common mode signal of the MES inputs. VREF is a voltage that assures the inputs of the instrumentation amplifier remain in the acceptable range of common mode input voltage. VREF is typically half of the power supply voltage powering the instrumentation amplifier. R31 is typically very large (much greater than the electrode source impedance) and is used to provide bias current to the inputs of the instrumentation amplifier. C45 assures that the common mode return node does not have any RF or very high audio frequency noise. C46 and R32 drive the common mode return node with a voltage which is the average (common mode) of the inverting (−) and non-inverting (+) input of the instrumentation amplifier. This 'bootstrapped' design minimizes the impact of the filtering components on the overall common mode rejection of the amplifier. The response of the instrumentation amplifier to the anticipated MES signal artifacts should be well behaved; i.e., the MES_Signal output may be contaminated by the artifact, but it should not invoke a slow overload recovery process or otherwise inject current into the input filtering networks.

The digital signal processing, performed by the microcontroller 24, will include the gating (suspension) of MES signal computations during and immediately following the detection of high common mode signals (likely stimulus artifact). The digital signal processing is described in more detail later.

The results of the digital signal processing are sent via wireless telemetry link 50 (as shown in FIG. 6 for which a representative circuit is shown in FIG. 7) to the external device(s) and may also be monitored by other implanted devices.

e. The Lead Connection Header

According to one desirable technical feature, the MES processor 18 desirably includes a lead connection header 14 for connecting the lead(s) 12 that will enable reliable and easy replacement of the lead/electrode (see FIGS. 2A and 2B), and includes a small antenna 54 for use with the wireless telemetry feature.

The MES processor desirably incorporates a connection header (top header) 14 (see FIGS. 2A and 2B0 that is easy to use, reliable, and robust enough to allow multiple replacements of the MES processor after many years (e.g., more than ten years) of use. The surgical complexity of replacing an MES processor is usually low compared to the surgical complexity of correctly placing the implantable lead 12/electrode 16 in proximity to the target nerve/tissue and routing the lead 12 to the MES processor. Accordingly, the lead 12 and electrode 16 desirably has a service life of at least ten years with a probable service life of fifteen years or more. Based on the clinical application, the MES processor may not have this long a service life. The MES processor service life is largely determined by the number of charge-discharge cycles of the Lithium Ion battery 22, and is likely to be three to ten years, based on the usage of the device. Most desirably, the MES processor 18 has a service life of at least five years.

As described above, the MES processor preferably will use a laser welded titanium case. As with other active implantable medical devices using this construction, the implantable lead(s) 12 connect to the MES processor through a molded or cast polymeric connection header 14 (top header). Metal-ceramic or metal-glass feed-thrus maintain the hermetic seal of the titanium capsule while providing electrical contact to the two or more electrical contacts of the lead 12/electrode 16.

The standard implantable connectors may be similar in design and construction to the low-profile IS-1 connector system (per ISO 5841-3) or the IS-4 connector system which is still in draft form. The IS-1 connectors have been in use since the late 1980s and have been shown to be reliable and provide easy release and re-connection over several MES processor replacements during the service life of a single recording lead. Full compatibility with the IS-1 standard or the IS-4 draft, and mating with recording leads, is not a requirement for the MES processor.

The MES processor connection system may include a modification of the IS-4 connector system, which shrinks the axial length dimensions while keeping the format and radial dimensions of the IS-4. For application with more than two electrode conductors, the top header 14 may incorporate one or more connection receptacles each of which accommodate leads with typically four conductors.

These connectors can be similar to the banded axial connectors used by other multi-polar MES processors or may follow the guidance of the draft IS-4 implantable connector standard. The design of the MES processor housing and header 14 preferably includes provisions for adding the additional feed-thrus and larger headers for such indications.

The inclusion of the UHF antenna 54 for the wireless telemetry inside the connection header (top header) 14 is necessary as the shielding offered by the titanium case will severely limit (effectively eliminate) radio wave propagation through the case. The antenna 54 connection will be made through a feed-thru similar to that used for the electrode connections. Alternatively, the wireless telemetry signal may be coupled inside the MES processor onto a electrical signal input channel and coupled to the antenna 54 with passive filtering/coupling elements/methods in the connection header 14.

f. The Microcontroller

According to one desirable technical feature, the MES processor 18 desirably uses a standard, commercially available micro-power, flash programmable microcontroller 24 or processor core in an application specific integrated circuit (ASIC). This device (or possibly more than one such device for a computationally complex application) and other large semiconductor components may have custom packaging such as chip-on-board, solder flip chip, or adhesive flip chip to reduce circuit board real estate needs.

Figure 10:
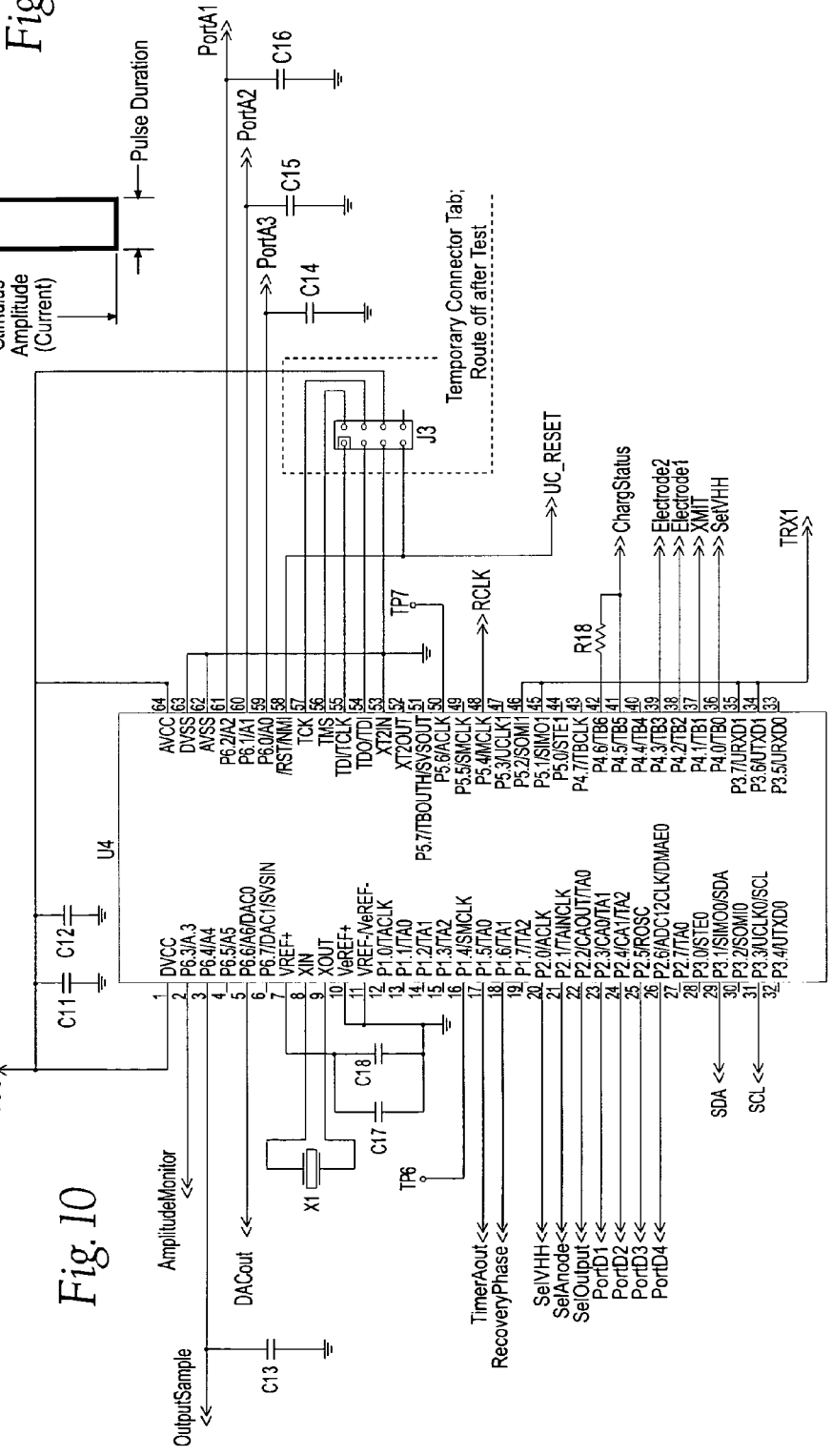
FIG. 10 is a circuit diagram showing a possible circuit for the microcontroller used with the MES processor shown in FIGS. 2A and 2B.

A circuit diagram showing a representative configuration for the microcontroller 24 is shown in FIG. 10. It is to be appreciated that modifications to this circuit diagram configuration which produce the same or similar functions as described are within the scope of the invention.

g. Power Management Circuitry

According to one desirable technical feature, the MES processor 18 desirably includes efficient power management circuitry 106 as an element of the MES processor circuitry 20 shown in FIG. 6. The power management circuitry 106 is generally responsible for the efficient distribution of power, the recovery of power from the RF magnetic field, and for charging and monitoring the Lithium Ion battery 22. In addition, the operation of the MES processor 18 can be described in terms of having operating modes as relating to the function of the power management circuitry. These modes may include, but are not limited to Active and Charging, Active, and Dormant. These modes will be described below in terms of the principles of operation of the power management circuitry using possible circuit diagrams shown in FIGS. 11 and 12.

Figure 11:
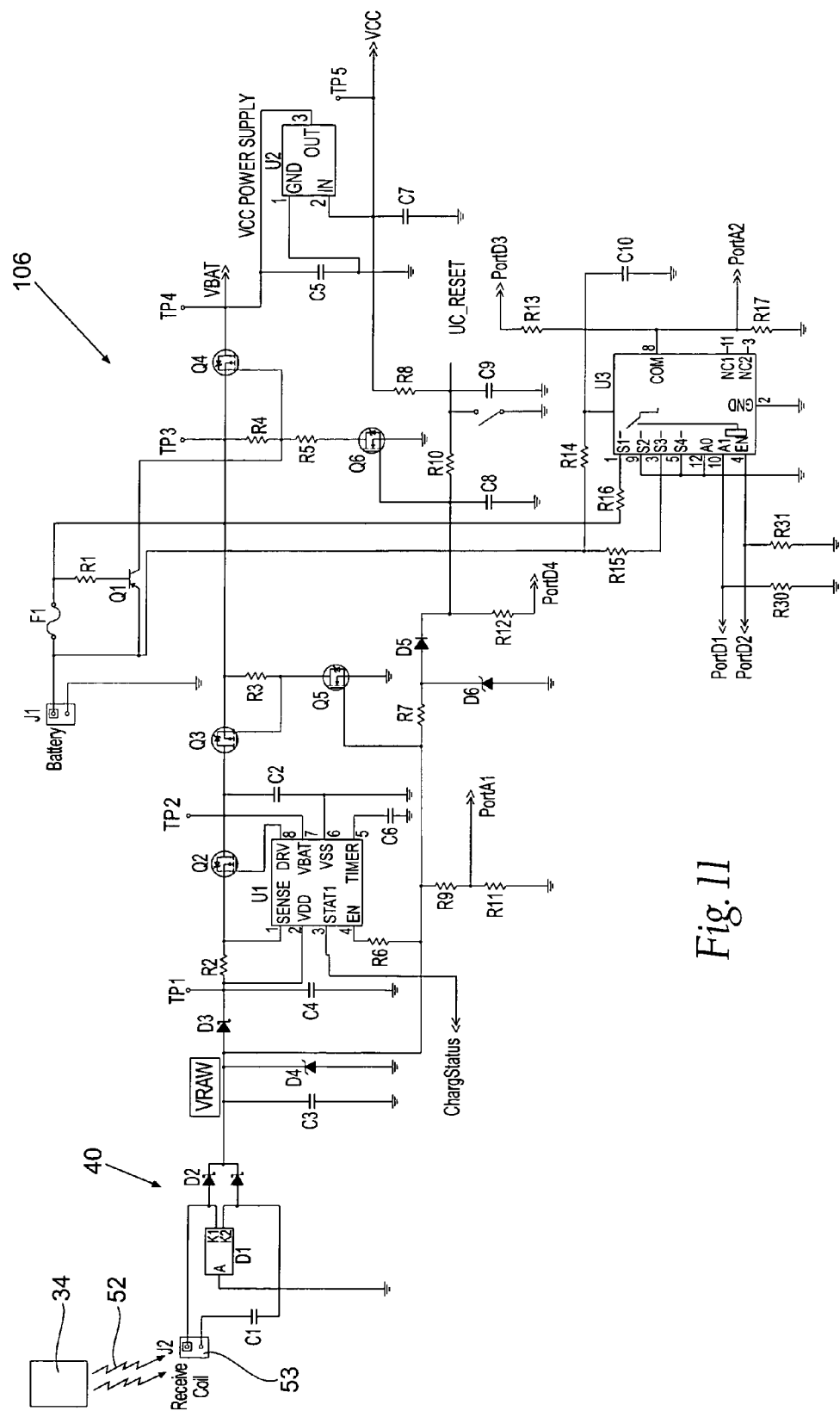
FIG. 11 is a circuit diagram showing one possible option for a power management sub-circuit where the sub-circuit includes MOSFET isolation between the battery and charger circuit, the power management sub-circuit being a part of the MES processor circuit shown in FIG. 6.
Figure 12:
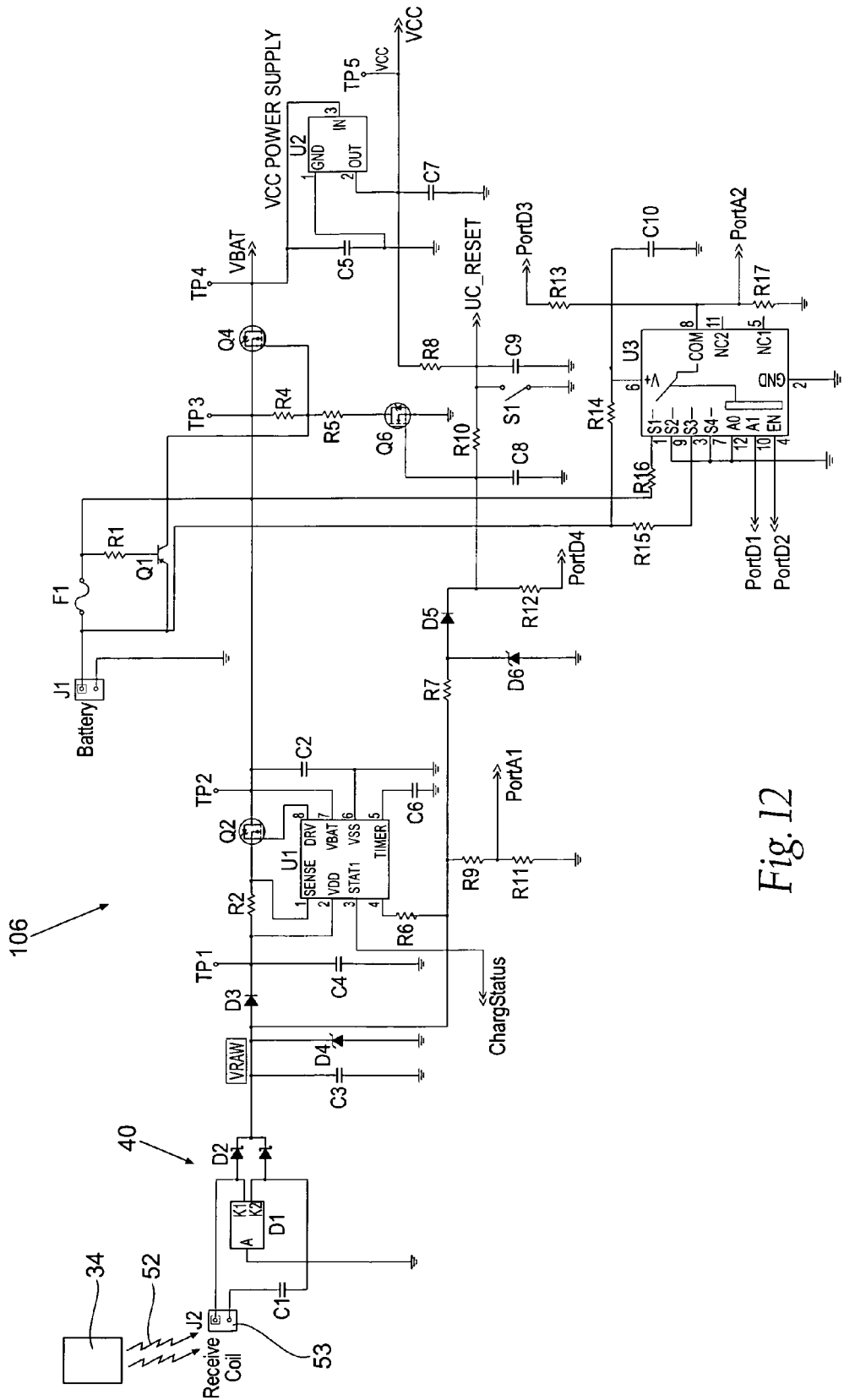
FIG. 12 is a circuit diagram showing a second possible option for a power management sub-circuit where the sub-circuit does not include MOSFET isolation between the battery and charger circuit, the power management sub-circuit being a part of the MES processor circuit shown in FIG. 6.

FIG. 11 shows one possible power management sub-circuit 106 having MOSFET isolation between the battery 22 and the charger circuit. FIG. 12 shows another possible power management sub-circuit 106 without having MOSFET isolation between the battery 22 and the charger circuit. In the circuit without the isolation MOSFET (see FIG. 12), the leakage current of the disabled charge control integrated circuit chip (U1) must be very low to prevent this leakage current from discharging the battery 22 in all modes (including the Dormant Mode). Except as noted, the description of these modes applies to both circuits.

i. Active and Charging Mode

The Active and Charging mode occurs when the MES processor 18 is being charged. In this mode, the MES processor is active, i.e., the microcontroller 24 is powered and coordinating wireless communications and may be timing and controlling the acquisition and processing of myoelectric signals. The MES processor 18 may be communicating with the MES processor charger 34 concerning the magnitude of the battery voltage and the DC voltage recovered from the RF magnetic field. The charger 34 uses this data for two purposes: to provide feedback to the user about the proximity of the charging coil 35 (see FIGS. 4A and 4B) to the implanted MES processor 18, and to increase or decrease the strength of the RF magnetic field. This, in turn, minimizes the power losses and undesirable heating of the MES processor.

While in the Active and Charging mode, the power management circuitry 40 serves one or more of the following primary functions: (1) provides battery power to the rest of the MES processor circuitry; (2) recovers power from the RF magnetic field generated by the MES processor charger 34; (3) provides controlled charging current (from the recovered power) to the battery 22; and (4) communicates with the MES processor charger 34 via the wireless telemetry link 38 to provide feedback to the user positioning the charging coil 35 over the MES processor, and to cause the MES processor charger 34 to increase or decrease the strength of its RF magnetic field for optimal charging of the MES processor battery 22 (e.g., a Lithium Ion battery).

(a) Principles of Operation, Active and Charging Mode i(a)(1) As FIGS. 11 and 12 show, RF voltage is induced in the Receive Coil 53 by the RF magnetic field 52 of the MES processor charger 34 i(a)(2) Capacitor C1 is in series with the Receive Coil 53 and is selected to introduce a capacitive reactance that compensates (subtracts) the inductive reactance of the Receive Coil i(a)(3) D1-D2 form a full wave rectifier that converts the AC voltage recovered by the Receive. Coil 53 into a pulsating DC current flow i(a)(4) This pulsating DC current is smoothed (filtered) by C3 (this filtered DC voltage is labeled VRAW)

i(a)(5) D4 is a zener diode that acts as a voltage limiting device (in normal operation, D4 is not conducting significant current)

i(a)(6) D3 prevents the flow of current from the battery 22 from preventing the correct operation of the Charge Management Circuitry once the voltage recovered from the RF magnetic field is removed. Specifically, current flow from the battery [through Q3 (turned ON), in the case for the circuit of FIG. 11] through the body diode of Q2 would hold ON the charge controller IC (U1). This additional current drain would be present in all modes, including dormant, and would seriously limit battery operating life. Additionally, this battery current pathway would keep Q6 turned ON even if the magnetic reed switch (S1) were closed; thus preventing the isolation of the IPG circuitry from the battery in the dormant mode.

i(a)(7) In FIG. 11, D3 is desirably a schottky diode because of the lower forward voltage drop; whereas it is desirably a conventional silicone diode in FIG. 12 because of the lower reverse voltage leakage current.

i(a)(8) U1, Q2, R2, C4, C6, and C2 form the battery charger sub-circuit

U1 is a micropower, Lithium Ion Charge Management Controller chip implementing a constant current phase and constant voltage phase charge regime. This chip desirably incorporates an internal voltage reference of high accuracy (+/−0.5%) to establish the constant voltage charge level. U1 performs the following functions:

monitors the voltage drop across a series resistor R2 (effectively the current charging the battery 22) to control the current delivered to the battery through the external pass transistor Q2. U1 uses this voltage across R2 to establish the current of the constant current phase (typically the battery capacity divided by five hours), and decreases the current charging the battery as required to limit the battery voltage and effectively transition from constant current phase to constant voltage phase as the battery voltage approaches the terminal voltage, i(a)(9) U1 also includes provisions for timing the duration of the constant current and constant voltage phases and suspends the application of current to the battery 22 if too much time is spent in the phase. These fault timing features of U1 are not used in normal operation.

i(a)(10) In this circuit, the constant voltage phase of the battery charging sequence is timed by the microcontroller 24 and not by U1. The microcontroller monitors the battery voltage and terminates the charging sequence (i.e., tells the MES processor charger 34 that the MES processor battery 22 is fully charged) after the battery voltage has been in the constant voltage region for greater than a fixed time period (e.g., 15 to 20 minutes).

i(a)(11) In FIG. 11, Q3 and Q5 are turned ON only when the charging power is present. This effectively isolates the charging circuit from the battery 22 when the externally supplied RF magnetic field 52 is not present and providing power to charge the battery.

i(a)(12) In FIG. 12, U1 is always connected to the battery 22, and the disabled current of this chip is a load on the battery 22 in all modes (including the dormant mode). This, in turn, is a more demanding requirement on the current consumed by U1 while disabled.

i(a)(13) F1 is a fuse that protects against long-duration, high current component failures. In all anticipated transient high current failures, (i.e., soft failures that cause the circuitry to consume high current levels and thus dissipate high power levels; but the failure initiating the high current flow is not permanent and the circuit will resume normal function if the circuit is removed from the power source before damage from overheating occurs), the VBAT circuitry will disconnect the battery 22 from the temporary high load without blowing the fuse. The specific sequence is:

(1) High current flows into a component(s) powered by VBAT (most likely the VHH power supply or an element powered by the VCC power supply).
(2) The voltage drop across the fuse will (prior to the fuse blowing) turn ON Q1 (based on the current flow through the fuse causing a 0.5V to 0.6V drop across the resistance of F1).
(3) The collector current from Q1 will turn off Q4.
(4) VBAT drops very quickly and, as a direct result, VCC falls. In turn, the voltage on the PortD4 IO pin from the microcontroller voltage falls as VCC falls, through the parasitic diodes in the microcontroller 24. This then pulls down the voltage across C6 as it is discharged through R12.
(5) The MES processor is now stable in the Dormant Mode, i.e., VBAT is disconnected from the battery 22 by a turned OFF Q4. The only load remaining on the battery is presented by the charging circuit and by the analog multiplexer (switches) U3 that are used to direct an analog voltage to the microcontroller 24 for monitoring the battery voltage and (by subtracting the voltage after the resistance of F1) an estimate of the current consumption of the entire circuit. A failure of these voltage monitoring circuits is not protected by the fuse, but resistance values limit the current flow to safe levels even in the event of component failures. A possible source of a transient high-current circuit failure is the SCR latchup or supply-to-ground short failure of a semiconductor device directly connected to VBAT or VCC.

R9 & R11 form a voltage divider to convert VRAW (approximately zero volts to eight volts) into the voltage range of the microcontroller's A-D inputs (used for closed loop control of the RF magnetic field strength), i(a)(14) R8 and C9 form the usual R-C reset input circuit for the microcontroller 24; this circuit causes a hardware reset when the magnetic reed switch (S1) is closed by the application of a suitable static magnetic field for a short duration, (a)(15) R10 and C8 form a much slower time constant that allows the closure of the reed switch by the application of the static magnetic field for a long duration to force the MES processor into the Dormant mode by turning OFF Q6 and thus turning OFF Q4. The use of the magnetic reed switch for resetting the microcontroller 24 or forcing a total MES processor shutdown (Dormant mode) may be a desirable safety feature.

ii. Active Mode

The Active mode occurs when the MES processor 18 is not being charged and it is operating normally. In this mode, the MES processor may be acquiring and processing sensed signals or it may be waiting for the next request to sample myoelectric signals in response to a timed sampling sequence or a telemetry command from an external controller. In this mode, the MES processor is active (microcontroller 24 is powered and coordinating wireless communications and may be timing & controlling the acquisition and processing of myoelectric signals). There is no MES processor charger 34 present.

ii(a) Principles of Operation, Active Mode

In the Active mode, there is no MES processor charger 34 present, and thus no DC voltage recovered by Receive Coil 53, D1, D2, and C3. In FIG. 11, the lack of DC current from VRAW means that Q5 is held off. This, in turn, holds Q3 off and the charging circuitry is isolated from the battery 22. In FIG. 12, the lack of DC current from VRAW means that U1 is disabled. This, in turn, keeps the current drain from the battery 22 to an acceptably low level, typically less than 1 μA.

iii. Dormant Mode

The Dormant mode occurs when the MES processor 18 is not being charged and it is completely disabled (powered down). In this mode, power is not being supplied to the microcontroller 24 or other enabled circuitry. This is the mode for the long-term storage of the MES processor before or after implantation. The Dormant mode may only be exited by placing the MES processor into the Active and Charging mode by placing the MES processor charging coil 35 of a functional MES processor charger 34 in close proximity to the MES processor 18.

iii(a) Principles of Operation, Dormant Mode

In the Dormant mode, there is no MES processor charger 34 present, and thus no DC voltage recovered by Receive Coil 53, D1, D2, and C3. VBAT is not delivered to the remainder of the MES processor circuitry because Q4 is turned off. The Dormant mode is stable because the lack of VBAT means that VCC is also not present, and thus Q6 is not held on through R8 and R10. Thus the battery 22 is completely isolated from all load circuitry (the VCC power supply and the VHH power supply).

The Dormant mode is entered through the application of a long magnet placement over S1 (magnetic reed switch) or through the reception of a command by the wireless telemetry. In the case of the telemetry command, the PortD4, which is normally configured as a microcontroller input, is configured as a logic output with a logic low (0) value. This, in turn, discharges C8 through R12 and turns off Q6; which, in turn, turns off Q4 and forces the MES processor into the Dormant mode. Note that R12 is much smaller in value than R10, thus the microcontroller 24 can force C8 to discharge even though VCC is still present.

In FIG. 11, the lack of DC current from VRAW means that Q5 is held off. This, in turn, holds Q3 off and the charging circuitry is isolated from the battery 22. Also, Q4 was turned off. In FIG. 12, the lack of DC current from VRAW means that U1 is disabled. This, in turn, keeps the current drain from the battery 22 to an acceptably low level, typically less than 1 μA.

2. Representative MES Processor Circuitry

FIG. 6 shows a representative circuit 20 for the MES processor 18 that takes into account the desirable technical features discussed above.

The circuit 20 can be grouped into functional blocks, which generally correspond to the association and interconnection of the electronic components. FIG. 6 shows a block diagram that provides an overview of a representative desirable MES processor design.

In FIG. 6, seven functional blocks are shown: (1) The Microprocessor or Microcontroller 24; (2) the Power Management Circuit 40 for the battery 22; (3) the VCC Power Supply 42; (4) the Input Coupling, EMC/ESD Networks 44; (5) the Instrumentation Amplifiers, 46; (6) the Bandpass filters 104; and (7) the Wireless Telemetry Circuit 50.

For each of these blocks, the associated functions, possible key components, and circuit description are now described.

a. The Microcontroller

The Microcontroller 24 is generally responsible for the following functions:

(1) The enabling and control of the instrumentation amplifiers and filtering circuitry, (2) The sequencing and timing of power management functions, (3) The monitoring of the battery voltage, the voltage recovered from the RF magnetic field 52 during the battery charging process, and the total circuit current consumption, VHH, and VCC, (4) The timing, control, and interpretation of commands to and from the wireless telemetry circuit, (5) The logging (recording) of patient usage data as well as clinician programmed MES processing parameters and limits, and configuration data, and (6) The digital processing of the MES signals into finished results (command values), into intermediate results, or into compressed data for communication via the wireless telemetry link.

The use of a microcontroller incorporating flash programmable memory allows the operating program (processing and/or compression algorithms) of the MES processor as well as the processing parameters, settings, and thresholds and usage history to be stored in non-volatile memory (data remains safely stored even if the battery 22 becomes fully discharged). Yet, the non-volatile memory can be erased and reprogrammed thousands of times during the life of the MES processor. The software (firmware) of the MES processor must be segmented to support the operation of the wireless telemetry routines while the flash memory of the microcontroller 24 is being erased and reprogrammed. Similarly, the VCC power supply 42 must support the power requirements of the microcontroller 24 during the flash memory erase and program operations.

The digital signal processing algorithms that will be employed may include comparison of processed values with pre-defined thresholds. The processing value may include average of rectified value, root-mean-square (rms) value, mean-squared value, number of zero crossings, ratio of energy in one band of frequencies to the energy in another band, rate of change (first order time derivative) of rectified value or rms, Finite Impulse Response (FIR) filtering, Infinite Impulse Response 9IIR) filtering, or one of several adaptive filtering algorithms.

The Components of the Microcontroller Circuit may include:

(1) A single chip microcontroller 24. This component may be a member of the Texas Instruments MSP430 family of flash programmable, micro-power, highly integrated mixed signal microcontroller. Likely family members to be used include the MSP430F1610, MSP430F1611, MSP430F1612, MSP430F168, and the MSP430F169. Each of these parts has numerous internal peripherals, and a micropower internal organization that allows unused peripherals to be configured by minimal power dissipation, and an instruction set that supports bursts of operation separated by intervals of sleep where the microcontroller suspends most functions.

(2) A miniature, quartz crystal (X1) for establishing precise timing of the microcontroller. This may be a 32.768 KHz quartz crystal.

(3) Miscellaneous power decoupling and analog signal filtering capacitors.

b. Power Management Circuit

The Power Management Circuit 40 is generally responsible for the following functions:

(1) recover power from the Receive Coil 53, (2) control delivery of the Receive Coil power to recharge the Lithium Ion secondary battery 22, (3) monitor the battery voltage during charge and discharge conditions, (4) communicate (through the wireless telemetry link 38) with the externally mounted MES processor charger 34 to increase or decrease the strength of the RF magnetic field 52 for optimal charging of the battery, (5) suspend stimulation when the battery voltage becomes very low, and/or suspend all operation (go into the Dormant Mode) when the battery voltage becomes critically low, (6) disable (with single fault tolerance) the delivery of charging current to the battery 22 in overcharge conditions, (7) communicate (through the wireless telemetry link 38) with the external equipment the charge status of the battery 22, (8) prevent (with single fault tolerance) the delivery of excessive current from the battery 22, (9) provide battery power to the rest of the circuitry of the MES processor, i.e., VCC and VHH power supplies,

(10) provide isolation of the Lithium Ion battery 22 from other circuitry while in the Dormant Mode,

(11) provide a hard microprocessor reset and force entry into the Dormant Mode in the presence of a pacemaker magnet (or comparable device), and

(12) provide the microcontroller 24 with analog voltages with which to measure the magnitude of the recovered power from the RF magnetic field 52, the battery voltage, and the appropriate battery current flow (drain and charge).

The Components of the Power Management Circuit may include:

(1) The Receive Coil 53, which desirably comprises a multi-turn, fine copper wire coil near the inside perimeter of the MES processor 18. Preferably, the receive coil 53 includes a predetermined construction, e.g., desirably 250 to 350 turns, and more desirably 300 turns of four strands of #40 enameled magnetic wire, or the like. The maximizing of the coil's diameter and reduction of its effective RF resistance allows necessary power transfer at typical implant depth of about one centimeter.

(2) A micropower Lithium Ion battery charge management controller IC (integrated circuit); such as the MicroChip MCP73843-41, or the like.

(3) Low on resistance, low threshold P channel MOSFETs with very low off state leakage current (Q2, Q3, and Q4).

(4) Analog switches (or an analog multiplexer) U3.

(5) Logic translation N-channel MOSFETs (Q5 & Q6) with very low off state leakage current.

c. The VCC Power Supply

The VCC Power Supply 42 is generally responsible for the following functions:

(1) Provide the microcontroller 24 and other circuitry with regulated 3.3VDC (typical) despite changes in the Lithium Ion battery voltage.

The Components of the VCC Power Supply might include:

(1) Micropower, low drop out, linear voltage regulator; e.g., Microchip NCP1700T-3302, Maxim Semiconductor MAX1725, or Texas Instruments TPS79730, or the like.

The characteristics of the VCC Power Supply might include:

(1) quiescent current, i.e., the current wasted by the power supply in its normal operation. This value should be less than a few microamperes, and (2) drop-out voltage, i.e., the minimal difference between the VBAT supplied to the VCC power supply and its output voltage. This voltage may be less than about 100 mV even at the current loads presented by the transmitter of the wireless telemetry circuitry.

d. Input Coupling & EMC/ESD Networks

Each MES channel has (typically) two differential inputs from a bipolar electrode located near a muscle or other excitable nervous system tissue. These two signal, in turn, may also have voltage transients caused by Electrostatic Discharges (ESD) to the body near the implanted MES processor or electrodes. These transient voltages can damage the instrumentation amplifiers and must be limited by passive components near the electrode connections. This function is typically provided by small signal silicon diodes back biased to the supply rails of the instrumentation amplifier or by silicone transient voltage suppressor diodes (similar to back-to-back zener diodes).

The presence of radiofrequency signals on the MES electrode inputs (radiofrequency interference (RFI)) is well outside the frequency range of the MES signals. However, large RFI signals can introduce non-linearities in the instrumentation amplifiers and cause an artifact that is within the passband of the MES signals. This RFI must be attenuated to an acceptable level before it is applied to the input of the instrumentation amplifier. This is typically accomplished by using passive filtering components; including small ferrite L-R-C networks as well as lumped components.

The electrodes themselves may or may not be capable of supporting the bias current of the instrumentation amplifier without developing an offset (polarization) voltage. This is a function of the electrode material used and the bias currents involved. An input coupling capacitors to block the DC current from the instrumentation amplifier from flowing through the electrodes may be used resolve this problem.

e. Instrumentation Amplifiers

The instrumentation amplifiers 46 serve two functions: to amplify the differential voltage between the two bipolar electrode connections of a given channel, and the reject (given no gain) to the voltage that is common to both signals. The instrumentation amplifiers must accept signals with up to 200 mVpp of common mode noise. The instrumentation amplifiers must have a high differential impedance (the electrode circuit source impedances may typically be between 500 ohms and 2,000 ohms). The instrumentation amplifiers must have a very high common mode input impedance. The instrumentation amplifiers may have a provision for the microcontroller to program their gain.

A typical input signal will have an amplitude of 1 mVpp to 20 mVpp. The output signal will typically be about 1 Vpp. The instrumentation amplifiers must also have adequate gain-bandwidth product to provide the necessary gain and CMRR throughout the MES passband (approx. 10 Hz-500 Hz or 1 KHz).

f. Passband Filters

The bandpass filters 104 serve two functions: to eliminate (filter out) low frequency signals that have little MES content and may have a lot of artifact content; and to filter out signals (both MES and artifact) that are changing so fast as to confuse the sampling process (so called anti-alias filtering). It is anticipated that the digital signal processing algorithms will sample the MES signals at 1,000 or 2,000 samples per second. It is anticipated that relatively simple analog filters would be adequate for these purposes. More sophisticated, higher order filters may be used for the lowpass (high frequency attenuation, anti-aliasing) function.

g. Wireless Telemetry Circuit

The Wireless Telemetry circuit 50 is generally responsible for the following functions:

(1) Provide reliable, bidirectional communications (half duplex) with an external controller, programmer, or charger 34, for example, via a VHF-UHF RF link (likely in the 4.02 MHZ to 405 MHz MICS band per FCC 47 CFR Part 95 and the Ultra Low Power-Active Medical Implant (AMI) regulations of the European Union). This circuit will look for RF commands at precisely timed intervals (e.g., twice a second), and this function must consume very little power. Much less frequently this circuit will transmit to the external controller. This function should also be as low power as possible; but will represent a lower total energy demand than the receiver in most of the anticipated applications. The RF carrier is amplitude modulated (on-off keyed) with the digital data. Serial data is generated by the microcontroller 24 already formatted and timed. The wireless telemetry circuit 50 converts the serial data stream into a pulsing carrier signal during the transit process; and it converts a varying RF signal strength into a serial data stream during the receive process.

The Components of the Wireless Telemetry Circuit 50 (see FIG. 7) might include:

(1) a crystal controlled, micropower transceiver chip such as the AMI Semiconductor AMIS-52100 (U6). This chip is responsible for generating the RF carrier during transmissions and for amplifying, receiving, and detecting (converting to a logic level) the received RF signals. The transceiver chip must also be capable of quickly starting and stopping operation to minimize power consumption by keeping the chip disabled (and consuming very little power) the majority of the time; and powering up for only as long as required for the transmitting or receiving purpose.

(2) The transceiver chip has separate transmit and receive ports that must be switched to a single antenna/feedthru. This function is performed by the transmit/receive switch (U5) under microcontroller control via the logic line XMIT. The microcontroller 24 controls the operation of the transceiver chip via an I²C serial communications link. The serial data to and from the transceiver chip may be handled by a UART or a SPI peripheral of the microcontroller. The message encoding/decoding and error detection may be performed by a separate, dedicated microcontroller; else this processing will be time shared with the other tasks of the only microcontroller.

The various inductor and capacitor components (U6) surrounding the transceiver chip and the transmit/receive switch (U5) are impedance matching components and harmonic filtering components, except as follows:

(1) X2, C33 and C34 are used to generate the crystal controlled carrier, desirably tuned to the carrier frequency divided by thirty-two, (2) L4 and C27 form the tuned elements of a VCO (voltage controlled oscillator) operating at twice the carrier frequency, and (3) R20, C29, and C30 are filter components of the PLL (phase locked loop) filter.

II. Representative Indications

Due to its technical features, the MES processor 18 as just generally described can be used to acquire and process myoelectric signals into instruction signals. These instruction signals can then be sent using wireless telemetry to a control device, such as a controller for an artificial limb, or to an implantable pulse generator, in order to provide beneficial results in diverse therapeutic and functional restorations indications.

For example, in the field of urology, possible indications for use of the MES processor 18 include the detection of excessive or inadequate nervous system activity to invoke or control the application of energy or drugs for the treatment of (i) urinary and fecal incontinence; (ii) micturition/retention; (iii) restoration of sexual function; (iv) defecation/constipation; (v) pelvic floor muscle activity; and/or (vi) pelvic pain.

The MES processor 18 can be used for the detection of excessive or inadequate nervous system activity to invoke or control the application of energy or drugs (e.g., deep brain stimulation) for the treatment of in the treatment of (i) Parkinson's disease; (ii) multiple sclerosis; (iii) essential tremor; (iv) depression; (v) eating disorders; (vi) epilepsy; and/or (vii) minimally conscious state.

The MES processor 18 can be used for the detection of excessive or inadequate nervous system activity to invoke or control the application of energy or drugs in the treatment of pain, e.g., (i) peripheral neuropathy; and/or (ii) cancer.

The MES processor 18 can be used for the detection of excessive or inadequate nervous system activity to invoke or control the application of energy or drugs (e.g., vagal nerve stimulation) for control of epilepsy, depression, or other mood/psychiatric disorders.

The MES processor 18 can be used for the detection of excessive or inadequate nervous system activity to invoke or control the application of energy or drugs for the treatment of obstructive sleep apnea.

The MES processor 18 can be used for the detection of excessive or inadequate nervous system activity to invoke or control the application of energy or drugs to prevent reflux or to reduce appetite or food consumption.

The MES processor 18 can be used for the detection of excessive or inadequate nervous system activity to invoke or control the application of energy or drugs in functional restorations indications such as the restoration of motor control, to restore (i) impaired gait after stroke or spinal cord injury (SCI); (ii) impaired hand and arm function after stroke or SCI; (iii) respiratory disorders; (iv) swallowing disorders; (v) sleep apnea; and/or (vi) neurotherapeutics, allowing individuals with neurological deficits, such as stroke survivors or those with multiple sclerosis, to recover functionally.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

We claim:

1. A system comprising:
   a lead configured to be implanted in a tissue of a patient;
   at least one electrode electrically coupled to the lead;
   an electrical signal processor electrically coupled to the lead, wherein the electrical signal processor is configured to be implanted in tissue remote from the at least one electrode, the electrical signal processor comprising:
      a housing, wherein the housing comprises a header,
      electrical signal sensing circuitry positioned within the housing, wherein the electrical signal sensing circuitry is configured to acquire electrical signals from the at least one electrode,
      a rechargeable power source positioned within the housing and configured to supply power to the electrical signal processor,
      a receive coil positioned within the housing and configured to transcutaneously receive a radio frequency magnetic field configured to recharge the rechargeable power source, and
      an antenna positioned within the header of the housing and configured to communicate via radio frequency wireless telemetry; and
   an external programmer configured to generate the radio frequency magnetic field and transcutaneously transmit the radio frequency magnetic field to the receive coil of the electrical signal processor to recharge the rechargeable power source, wherein the radio frequency magnetic field is defined by a frequency between about 30 KHz and about 300 KHz, and wherein the external programmer is further configured to communicate via the radio frequency wireless telemetry with the electrical signal processor, wherein the radio frequency wireless telemetry uses a frequency between about 402 MHz and about 405 MHz.

2. The system of claim 1, wherein the external programmer is configured to transcutaneously transmit the radio frequency magnetic field to the electrical signal processor to recharge the rechargeable power source and simultaneously communicate with the electrical signal processor via the radio frequency wireless telemetry.

3. The system of claim 1, wherein the external programmer is configured to initiate electrical signal sensing by the electrical signal sensing circuitry to acquire the electrical signals.

4. The system of claim 1, wherein the external programmer comprises a charging coil, the charging coil comprising between about 150 turns and about 250 turns of six strands of number 36 enameled magnetic wire.

5. The system of 4, wherein the charging coil has a diameter of between about 40 mm and about 60 mm, and a thickness as measured perpendicular to a mounting plane of between about 2 mm and about 5 mm.

6. The system of claim 1, further comprising: an implantable pulse generator configured to generate electrical stimulation delivery to the patient, wherein the external programmer is configured to activate, via the radio frequency wireless telemetry, the implantable pulse generator to generate the electrical stimulation.

7. The system of claim 6, wherein the external programmer is configured to allow the patient to adjust only predetermined characteristics defining the electrical stimulation.

8. The system of claim 1, wherein the external programmer is configured to communicate with the electrical signal processor via the radio frequency wireless telemetry at a distance of about two meters away from the electrical signal processor.

* * * * *